US008367890B2

(12) United States Patent
D'Halluin et al.

(10) Patent No.: US 8,367,890 B2
(45) Date of Patent: *Feb. 5, 2013

(54) METHODS AND MEANS FOR REMOVAL OF A SELECTED DNA SEQUENCE

(75) Inventors: Kathleen D'Halluin, Mariakerke (BE); Rene Ruiter, Heusden (BE)

(73) Assignee: Bayer Cropscience N.V., Diegem (BE)

( * ) Notice: Subject to any disclaimer, the term of this patent is extended or adjusted under 35 U.S.C. 154(b) by 721 days.

This patent is subject to a terminal disclaimer.

(21) Appl. No.: 12/442,727

(22) PCT Filed: Sep. 20, 2007

(86) PCT No.: PCT/EP2007/008342
§ 371 (c)(1),
(2), (4) Date: Mar. 25, 2009

(87) PCT Pub. No.: WO2008/037436
PCT Pub. Date: Apr. 3, 2008

(65) Prior Publication Data
US 2010/0050295 A1 Feb. 25, 2010

Related U.S. Application Data

(60) Provisional application No. 60/828,042, filed on Oct. 3, 2006.

(30) Foreign Application Priority Data

Sep. 28, 2006 (EP) .................................... 06020370

(51) Int. Cl.
C12N 15/62 (2006.01)
A01H 5/00 (2006.01)
(52) U.S. Cl. .......................... 800/278; 800/298; 435/419
(58) Field of Classification Search .................. None
See application file for complete search history.

(56) References Cited

U.S. PATENT DOCUMENTS

| 6,407,314 | B1 | 6/2002 | Oldenhof |  |
|---|---|---|---|---|
| 2005/0060769 | A1 | 3/2005 | Gilbertson |  |
| 2005/0172365 | A1* | 8/2005 | Puchta et al. | 800/294 |

FOREIGN PATENT DOCUMENTS

| EP | 0 317 509 | 5/1989 |
|---|---|---|
| EP | 0 790 311 A | 8/1997 |
| WO | 94/17176 | 8/1994 |
| WO | 94/18313 | 8/1994 |
| WO | 95/09233 | 4/1995 |
| WO | 96/14408 | 5/1996 |
| WO | 97/30166 | 8/1997 |
| WO | 00/46386 | 8/2000 |
| WO | 03/004659 | 1/2003 |
| WO | 03/080809 | 10/2003 |
| WO | 2004/013333 | 2/2004 |
| WO | 2004/067736 | 8/2004 |
| WO | 2005/049842 | 6/2005 |
| WO | WO 2005/049842 | * 6/2005 |
| WO | 2005/090581 | 9/2005 |
| WO | 2006/032426 | 3/2006 |
| WO | WO 2006/032426 | * 3/2006 |
| WO | 2006/105846 | 10/2006 |
| WO | WO 2006105946 | 10/2006 |

OTHER PUBLICATIONS

Rotman et al, A Novel Class of MYB Factors Controls Sperm-Cell Formation in Plants, 2005, Current Biology 15:244-248.*
Minami et al. Structure and some characteization of the gene ofr phenylalanine ammonia-lyase from rice plants, 1989, Eur. J. Biochem. 185:19-25.*
Accession No. BE225314 (Jul. 6, 2000) "RSCDS0127 Rice sperm cells lambda TriplEx2 cDNA library Oryza sativa Indica Group cDNA similar to polyubiquitin, mRNA sequence."
Accession No. BE225315 (Jul. 6, 2000) "RSCDS0128 Rice sperm cells lambda TriplEx2 cDNA library Oryza sativa Indica Group cDNA, mRNA sequence."
Accession No. BE225316 (Jul. 6, 2000) "RSCDS0129 Rice sperm cells lambda TriplEx2 cDNA library Oryza sativa Indica Group cDNA, mRNA sequence."
Accession No. BE225317 (Jul. 6, 2000) "RSCDS0130 Rice sperm cells lambda TriplEx2 cDNA library Oryza sativa Indica Group cDNA, mRNA sequence."
Accession No. BE225318 (Jul. 6, 2000) "RSCDS0131 Rice sperm cells lambda TriplEx2 cDNA library Oryza sativa Indica Group cDNA, mRNA sequence."
Accession No. BE225319 (Jul. 6, 2000) "RSCDS0132 Rice sperm cells lambda TriplEx2 cDNA library Oryza sativa Indica Group cDNA, mRNA sequence."
Accession No. BE225320 (Jul. 6, 2000) "RSCDS0133 Rice sperm cells lambda TriplEx2 cDNA library Oryza sativa Indica Group cDNA, mRNA sequence."
Accession No. BE225321 (Jul. 6, 2000) "RSCDS0134 Rice sperm cells lambda TriplEx2 cDNA library Oryza sativa Indica Group cDNA, mRNA sequence."
Accession No. BE225322 (Jul. 6, 2000) "RSCDS0135 Rice sperm cells lambda TriplEx2 cDNA library Oryza sativa Indica Group cDNA, mRNA sequence."
Accession No. BE225323 (Jul. 6, 2000) "RSCDS0136 Rice sperm cells lambda TriplEx2 cDNA library Oryza sativa Indica Group cDNA, mRNA sequence."
Accession No. BF475189 (Dec. 4, 2000) "ESTsub1A2(1) Subtracted rice sperm cells cDNA Library Oryza sativa Indica Group cDNA, mRNA sequence."
Accession No. Accession No. BF475190 (Dec. 4, 2000) ESTsub1A6(4) Subtracted rice sperm cells cDNA Library Oryza sativa Indica Group cDNA.

(Continued)

Primary Examiner — Elizabeth McElwain
(74) Attorney, Agent, or Firm — Hunton & Williams, LLP

(57) ABSTRACT

Alternative and/or improved methods are described for the exact removal of a selected subfragment from a DNA molecule by intrachromosomal recombination between two directly repeated DNA sequences using a rare-cleaving double stranded break inducing DNA endonuclease expressed under control of a micro-spore specific promoter. These methods can be applied for the exact exchange of a target DNA fragment for a DNA fragment of interest in plant cells and plants.

29 Claims, 8 Drawing Sheets

OTHER PUBLICATIONS

Accession No. Accession No. BF475191 (Dec. 4, 2000) ESTsub1B10(9) Subtracted rice sperm cells cDNA Library *Oryza sativa Indica* Group cDNA.
Accession No. Accession No. BF475192 (Dec. 4, 2000) ESTsub1B3(7) Subtracted rice sperm cells cDNA Library *Oryza sativa Indica* Group cDNA.
Accession No. Accession No. BF475193 (Dec. 4, 2000) "ESTsub1C8(14) Subtracted rice sperm cells cDNA Library *Oryza sativa Indica* Group cDNA similar to *Zea mays* hypersensitive-induced response protein (H1R1) mRNA, mRNA sequence."
Accession No. Accession No. BF475194 (Dec. 4, 2000) "ESTsub1B4(8) Subtracted rice sperm cells cDNA Library *Oryza sativa Indica* Group cDNA, mRNA sequence."
Accession No. Accession No. BF475195 (Dec. 4, 2000) "ESTsub1D1(17) Subtracted rice sperm cells cDNA Library *Oryza sativa Indica* Group cDNA, mRNA sequence."
Accession No. Accession No. BF475196 (Dec. 4, 2000) "ESTsub1B11(10) Subtracted rice sperm cells cDNA Library *Oryza sativa Indica* Group cDNA, mRNA sequence."
Accession No. Accession No. BF475197 (Dec. 4, 2000) "ESTsub 1E10(23) Subtracted rice sperm cells cDNA Library *Oryza sativa Indica* Group cDNA, mRNA sequence."
Accession No. Accession No. BF475198 (Dec. 4, 2000) "ESTsub1B12(11) Subtracted rice sperm cells cDNA Library *Oryza sativa Indica* Group cDNA, mRNA sequence."
Accession No. Accession No. BF475199 (Dec. 4, 2000) "ESTsub1G11(41) Subtracted rice sperm cells cDNA Library *Oryza sativa Indica* Group cDNA similar to NADH dependent Glutamate Synthase mRNA, mRNA sequence."
Accession No. Accession No. BF475200 (Dec. 4, 2000) "ESTsub1H3(43) Subtracted rice sperm cells cDNA Library *Oryza sativa Indica* Group cDNA, mRNA sequence."
Accession No. BF475201 (Dec. 4, 2000) "ESTsub1G1(34) Subtracted rice sperm cells cDNA Library *Oryza sativa Indica* Group cDNA, mRNA sequence."
Accession No. BF475202 (Dec. 4, 2000) "ESTsub1F12(33) Subtracted rice sperm cells cDNA Library *Oryza sativa Indica* Group cDNA, mRNA sequence."
Accession No. BF475203 (Dec. 4, 2000) "ESTsub1G4(37) Subtracted rice sperm cells cDNA Library *Oryza sativa Indica* Group cDNA, mRNA sequence."
Accession No. BF475204 (Dec. 4, 2000) "ESTsub1G8(39) Subtracted rice sperm cells cDNA Library *Oryza sativa Indica* Group cDNA, mRNA sequence."
Accession No. BF475205 (Dec. 4, 2000) "ESTsub1G10(40) Subtracted rice sperm cells cDNA Library *Oryza sativa Indica* Group cDNA, mRNA sequence."
Accession No. BF475206 (Dec. 4, 2000) "ESTsub1E5(22) Subtracted rice sperm cells cDNA Library *Oryza sativa Indica* Group cDNA, mRNA sequence."
Accession No. BF475207 (Dec. 4, 2000) "ESTsub1H6(45) Subtracted rice sperm cells cDNA Library *Oryza sativa Indica* Group cDNA, mRNA sequence."
Accession No. BF475208 (Dec. 4, 2000) "ESTsub1F8(30) Subtracted rice sperm cells cDNA Library *Oryza sativa Indica* Group cDNA, mRNA sequence."
Accession No. BF475209 (Dec. 4, 2000) "ESTsub1G2(35) Subtracted rice sperm cells cDNA Library *Oryza sativa Indica* Group cDNA, mRNA sequence."
Accession No. BF475210 (Dec. 4, 2000) "ESTsub2A1(49) Subtracted rice sperm cells cDNA Library *Oryza sativa Indica* Group cDNA, mRNA sequence."
Accession No. BF475211 (Dec. 4, 2000) "ESTsub2A2(50) Subtracted rice sperm cells cDNA Library *Oryza sativa Indica* Group cDNA, mRNA sequence."
Accession No. BF475212 (Dec. 4, 2000) "ESTsub2A3(51) Subtracted rice sperm cells cDNA Library *Oryza sativa Indica* Group cDNA, mRNA sequence."
Accession No. BF475213 (Dec. 4, 2000) "ESTsub2A5(53) Subtracted rice sperm cells cDNA Library *Oryza sativa Indica* Group cDNA, mRNA sequence."
Accession No. BF475214 (Dec. 4, 2000) "ESTsub2A7(54) Subtracted rice sperm cells cDNA Library *Oryza sativa Indica* Group cDNA, mRNA sequence."
Accession No. BF475215 (Dec. 4, 2000) "ESTsub2A10(55) Subtracted rice sperm cells cDNA Library *Oryza sativa Indica* Group cDNA, mRNA sequence."
Accession No. BF475216 (Dec. 4, 2000) "ESTsub2A11(56) Subtracted rice sperm cells cDNA Library *Oryza sativa Indica* Group cDNA, mRNA sequence."
Accession No. BF475217 (Dec. 4, 2000) "ESTsub2B2(58) Subtracted rice sperm cells cDNA Library *Oryza sativa Indica* Group cDNA, mRNA sequence."
Accession No. BF475218 (Dec. 4, 2000) "ESTsub2B3(59) Subtracted rice sperm cells cDNA Library *Oryza sativa Indica* Group cDNA similar to *Oryza sativa* polyubiquitin (Rubq1) mRNA, mRNA sequence."
Accession No. BF475219 (Dec. 4, 2000) "ESTsub2B6(60) Subtracted rice sperm cells cDNA Library *Oryza sativa Indica* Group cDNA, mRNA sequence."
Accession No. BF475220 (Dec. 4, 2000)"ESTsub2B11(63) Subtracted rice sperm cells cDNA Library *Oryza sativa Indica* Group cDNA similar to *Oryza sativa* inorganic pyrophosphatase (IPP) mRNA, mRNA sequence."
Accession No. BF475221 (Dec. 4, 2000) "ESTsub2B12(64) Subtracted rice sperm cells cDNA Library *Oryza sativa Indica* Group cDNA, mRNA sequence."
Accession No. BF475222 (Dec. 4, 2000) "ESTsub2C1(65) Subtracted rice sperm cells cDNA Library *Oryza sativa Indica* Group cDNA, mRNA sequence."
Accession No. BF475223 (Dec. 4, 2000) "ESTsub2C5(67) Subtracted rice sperm cells cDNA Library *Oryza sativa Indica* Group cDNA, mRNA sequence."
Accession No. BF475225 (Dec. 4, 2000) "ESTsub2C11(70) Subtracted rice sperm cells cDNA Library *Oryza sativa Indica* Group cDNA, mRNA sequence."
Accession No. BF475224 (Dec. 4, 2000) "ESTsub2C7(69) Subtracted rice sperm cells cDNA Library *Oryza sativa Indica* Group cDNA, mRNA sequence."
Accession No. BF475226 (Dec. 4, 2000) "ESTsub2C12(71) Subtracted rice sperm cells cDNA Library *Oryza sativa Indica* Group cDNA, mRNA sequence."
Accession No. BF475227 (Dec. 4, 2000) "ESTsub2D4(73) Subtracted rice sperm cells cDNA Library *Oryza sativa Indica* Group cDNA, mRNA sequence."
Accession No. BF475228 (Dec. 4, 2000) "ESTsub2D7(76) Subtracted rice sperm cells cDNA Library *Oryza sativa Indica* Group Cdna similar to *Porteresia coarctata* histone H3 mRNA, mRNA sequence."
Accession No. BF475229 (Dec. 4, 2000) "ESTsub2D8(77) Subtracted rice sperm cells cDNA Library *Oryza sativa Indica* Group cDNA similar to *Oryza astiva* thioredoxin h mRNA, mRNA sequence."
Accession No. BF475230 (Dec. 4, 2000) "ESTsub2E8(81) Subtracted rice sperm cells cDNA Library *Oryza sativa Indica* Group cDNA similar to *Oryza sativa* cysteine synthase (rcs3) mRNA, mRNA sequence."
Accession No. BF475231 (Dec. 4, 2000) "ESTsub2E10(82) Subtracted rice sperm cells cDNA Library *Oryza sativa Indica* Group cDNA, mRNA sequence."
Accession No. BF475232 (Dec. 4, 2000) "ESTsub2F2(83) Subtracted rice sperm cells cDNA Library *Oryza sativa Indica* Group cDNA, mRNA sequence."
Accession No. BF47533 (Dec. 4, 2000) "ESTsub2F3(84) Subtracted rice sperm cells cDNA Library *Oryza sativa Indica* Group cDNA, mRNA sequence."
Accession No. BF475234 (Dec. 4, 2000) "ESTsub2F4(85) Subtracted rice sperm cells cDNA Library *Oryza sativa Indica* Group cDNA, mRNA sequence."
Accession No. BF475235 (Dec. 4, 2000) "ESTsub2F7(88) Subtracted rice sperm cells cDNA Library *Oryza sativa Indica* Group cDNA, mRNA sequence."

Accession No. BF475236 (Dec. 4, 2000) "ESTsub2F12(90) Subtracted rice sperm cells cDNA Library *Oryza sativa Indica* Group cDNA, mRNA sequence."
Accession No. BF475237 (Dec. 4, 2000) "ESTsub2G9(96) Subtracted rice sperm cells cDNA Library *Oryza sativa Indica* Group cDNA, mRNA sequence."
Chilton and Que (2003) Plant Physiol. 133: 956.
Colleaux et al. (1988) Proc. Natl. Acad. Sci. USA 85: 6022.
Cordts et al. (2001) Plant J. 25(1): 103.
Drouaud et al. (2000) Sex Plant Reprod. 13: 29.
Engel et al. (2003) Plant J. 34: 697.
Galli et al. (2003) Genetics 165(4): 2093.
Guerche et al. (1999) Plant Mol. Biol. 40: 857.
Haerizadeh et al. (2006) Science 28(313): 496.
Hohn et al. (2001) Curr. Opin. Biotechnol. 12: 139.
Isalan et al. (2001) Nature Biotechnology 19: 656.
Kalderon et al. (1984) Cell 39: 499.
Kumar and Fladung (2001) Trends in Plant Science, 6: 155.
Liu et al. (1997) Proc. Natl. Acad. Sci. USA 94: 5525.

Marton et al. (2005) Science 307: 573.
Orel Nadiya et al. (2003) Plant Journal vol. 35, No. 5: 604.
Paszkowski et al. (1988) EMBO J. 7: 4021.
Puchta et al. (1996) Proc. Natl. Acad. Sci. U.S.A. 93: 5055.
Puchta et al. (2003) Journal of Plant Physiology vol. 160 No. 7: 743.
Puchta H. (2004) Journal of Experimental Botany vol. 56 No. 409: 1.
Raikhel(1992) Plant Physiol 100: 1627.
Rotman et al. (2005) Curr Biol. 15(3): 244.
Siebert and Puchta (2002) Plant Cell 14: 1121.
Singh et al. (2003) FEBS Lett. 542(1.
Tzfira et al. (2003) Plant Physiol. 133: 101 1.
Xu et al. (1998) Plant J. 13(6): 823.
Xu et al. (1999) Proc Natl Acad Sci USA 96(5): 2554.
Xu et al. (1999) Plant Mol. Biol. 39: 607.
Yang et al. (2005) Plant Physiol. 139(3): 1421.
Yu et al. (2005) Plant Physiology 139(4): 1853.

* cited by examiner

Continuation from Fig 1A

↓ Cross with receptor plant

↓ Selection of progeny for presence of SMG2

↓ Screening of progeny for absence of SmG1

Trait drs

GSP  DSBIE  3'  SMG2

↓ Cross with receptor plant

↓ Screening of progeny for absence of SMG2

↓

Trait drs

FIG 1B

METHODS AND MEANS FOR REMOVAL OF A SELECTED DNA SEQUENCE

CROSS-REFERENCE TO RELATED APPLICATIONS

This application is the U.S. National Stage filing of International Application No. PCT/EP2007/008342, filed Sep. 20, 2007, which claims priority to EP 06020370.0, filed Sep. 28, 2006, and U.S. Provisional Patent Application No. 60/828,042, filed Oct. 3, 2006, the disclosures of each of which are hereby incorporated by reference.

FIELD OF THE INVENTION

The current invention relates to improved or alternative methods and means that allow the efficient removal of a selected part of a DNA sequence of interest previously introduced into said plant, such as e.g. a selectable or screenable marker gene without resorting to in vitro culture during the removal step. The removal method can be used as part of a method for exact exchange in plant cells and plants of a target DNA sequence for a DNA sequence of interest through homologous recombination, whereby the selectable or screenable marker used during the homologous recombination phase for temporal selection of the gene replacement events can subsequently be removed without leaving a footprint and without resorting to in vitro culture during the removal step.

BACKGROUND ART

The removal of selected sub-fragments of foreign DNA introduced into plant cells or plants, but which have subsequently become obsolete or even unwanted, for various reasons, after introduction thereof, has been the subject of intensive research. Examples of such sequences are e.g. selectable marker genes which were necessary for the isolation of transgenic plants but which are no longer required in the mature plants. Methods to achieve efficient elimination thereof mostly rely on site-specific recombination or transposition (see e.g Hohn et al. (2001) Curr. Opin. Biotechnol. 12: 139-143).

Siebert and Puchta (Plant Cell (2002) 14: 1121-1131) described that transgenic sequences flanked by sites of a rare cutting restriction enzyme can be excised efficiently from the genome of a higher eukaryote by homologous recombination as well as by non-homologous end-joining.

WO03/004659 relates to recombination systems and to a method for removing nucleic acid sequence from the chromosomal DNA of eukaryotic organisms. The document also relates to transgenic organisms (preferably plants), containing the described systems or produced by the described methods.

WO05/090581 relates to constructs and methods for eliminating maker sequences from the genome of plants, based on dual-function selection marker which—depending on the employed compound—can act as both negative and counter-selection marker.

However the described methods mostly require the use of an in vitro culture method to identify or select those plant cells in which the deletion of the DNA sequences to be removed has effectively taken place and to regenerate a plant from such cells.

US patent application 2005/0060769 proposes a method to prepare a recombined transgenic Zea mays plant or plant cell from a first transgenic Zea mays plant cell, wherein the transgene in the recombinant plant or plant cell has an altered genetic structure relative to the genetic structure of the transgene in the first transgenic plant cell, due to homologous recombination-mediated transgene deletion.

WO97/30166 or U.S. Pat. No. 6,407,314 describe promoter fragments from a microspore-specific gene from tobacco that can be used for expression of genes in microspores.

WO06/105946 has described methods and means for the efficient removal of a selected part of a DNA sequence of interest previously introduced into the plant without resorting to in vitro culture during the removal step. The method described therein relied on the expression of a double stranded DNA break inducing rare cleaving endonuclease under the control of a microspore specific promoter. The microspore specific promoter which was specifically disclosed was the promoter region from the NTM 19 gene in tobacco as described in WO97/30166.

Provided herein are alternative methods and means for the removal of such a selected part of a DNA sequence as described hereinafter in the different detailed embodiment, examples, figures and claims.

Another problem that has been solved by the present invention concerns the targeted and exact exchange through homologous recombination of a target DNA sequence in a cell of a plant for a replacement DNA sequence without leaving footprints of the procedure, and without having to resort to in vitro culture methods after the initial step of homology recombination. To this end, the herein described methods for efficient removal of selected subsequence of a part of a DNA molecule previously inserted in the genome, preferably the nuclear genome of cells of a plant, through intrachromosomal homologous recombination can be conveniently used.

The need to control the site of transgene integration in plants has been recognized early on, and several methods have been developed in an effort to meet this need (for a review see Kumar and Fladung (2001) Trends in Plant Science, 6: 155-159). These methods mostly rely on homologous recombination-based transgene integration, a strategy which has been successfully applied in prokaryotes and lower eukaryotes (see e.g. EP0317509 or the corresponding publication by Paszkowski et al. (1988) EMBO J. 7: 4021-4026). However, for plants, the predominant mechanism for transgene integration is based on illegitimate recombination which involves little homology between the recombining DNA strands. A major challenge in this area is therefore the detection of the rare homologous recombination events, which are masked by the far more efficient integration of the introduced foreign DNA via illegitimate recombination.

One way of solving this problem is by selecting against the integration events that have occurred by illegitimate recombination, such as exemplified in WO94/17176.

Another way of solving the problem is by activation of the target locus through the induction of double stranded DNA breaks via rare-cutting endonucleases, such as I-SceI. This technique has been shown to increase the frequency of homologous recombination by at least two orders of magnitude using Agrobacteria to deliver the repair DNA to the plant cells (Puchta et al. (1996) Proc. Natl. Acad. Sci. U.S.A. 93: 5055-5060).

WO96/14408 describes an isolated DNA encoding the enzyme I-SceI. This DNA sequence can be incorporated in cloning and expression vectors, transformed cell lines and transgenic animals. The vectors are useful in gene mapping and site-directed insertion of genes.

WO00/46386 describes methods of modifying, repairing, attenuating and inactivating a gene or other chromosomal DNA in a cell through I-SceI double strand break. Also disclosed are methods of treating or prophylaxis of a genetic disease in an individual in need thereof. Further disclosed are chimeric restriction endonucleases.

Chilton and Que (Plant Physiol. (2003) 133: 956-965) and Tzifira et al. (Plant Physiol. (2003) 133: 1011-1023) report that T-DNA preferentially integrates in double stranded DNA breaks, artificially induced by the rare-cleaving enzymes I-SceI or I-CeuI. The reports also included donor T-DNA vectors which comprised a recognition site for the respective rare-cleaving enzyme.

However, the methods in the prior art frequently rely on the reformation or generation through homology recombination of an intact selectable or screenable marker gene.

WO06/105946 had also described a method for the exact exchange in plant cells and plants of a target DNA sequence for a DNA sequence of interest through homologous recombination, whereby the selectable or screenable marker used during the homologous recombination phase for temporal selection of the gene replacement events can subsequently be removed without leaving a foot-print and without resorting to in vitro culture during the removal step, employing the therein described method for the removal of a selected DNA by microspore specific expression of a double stranded break inducing rare cleaving endonuclease.

Therefore, there remains a need for alternative or improved methods which would allow targeted exchange of virtually any target DNA sequence by a replacement DNA. These and other problems are solved as described hereinafter in the different detailed embodiments of the invention, as well as in the claims.

SUMMARY OF THE INVENTION

In one embodiment of the invention a method is described for introduction of a DNA molecule of interest into the genome of a plant cell or plant followed by removal of a subsequence of the DNA molecule of interest, preferably comprising a selectable or screenable marker, comprising the steps of
  a. Introducing the DNA molecule of interest into the genome of the plant cell, the DNA molecule of interest comprising the subsequence of the DNA molecule flanked by two DNA sequences arranged in direct repeat and further comprising at least one recognition site for a rare cleaving double stranded DNA break inducing (DSBI) enzyme located in the vicinity of, preferably between, the two DNA sequences arranged in direct repeat;
  b. Selecting a plant cell wherein the DNA molecule of interest is integrated in the genome and regenerating a plant from the plant cell;
  c. Crossing the plant with a second plant comprising a DSBI enzyme encoding chimeric gene, the chimeric gene comprising the following operably linked DNA segments:
    i. a germline specific promoter fragment other than a promoter fragment selected from the nucleotide sequence of SEQ ID NO 3, such as a promoter fragment selected from the nucleotide sequence of SEQ ID No. 7;
    ii. a DNA region encoding a rare cleaving double stranded DNA break inducing enzyme recognizing the recognition site, such as an endonuclease selected from the group of I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I or a chimeric endonuclease comprising a Zn finger DNA binding domain and a DNA cleavage domain;
    iii. a transcription termination and polyadenylation region;
  d. Selecting a progeny plant (F1-plant) comprising the DNA molecule of interest and the DSBI enzyme encoding chimeric gene;
  e. Crossing the progeny plant with another plant;
  f. Selecting a population of progeny plants (F2-population) which comprises the DSBI enzyme encoding chimeric gene; and
  g. Selecting a progeny plant wherein subsequence of the DNA molecule has been deleted by homologous recombination between the two DNA sequences arranged in direct repeat and optionally
  h. Crossing the progeny plant wherein the subsequence of the DNA molecule has been deleted, with another plant; and
  i. Obtaining a population of progeny plants (F3-plants) and selecting plants which do not contain the rare cleaving DSBI enzyme encoding chimeric gene.

In another embodiment of the invention, a method is provided for exchanging a target DNA sequence in the genome, particularly the nuclear genome, of a plant for a DNA sequence of interest comprising the following steps:
  a. Inducing a first double stranded DNA break at a preselected site in the genome of a cell of a plant, the preselected site being located within the target DNA sequence or in the vicinity of the target DNA sequence;
  b. Introducing a DNA molecule of interest into the plant cell, the DNA molecule comprising
    i. The DNA sequence of interest located between two flanking DNA regions having at least 80% sequence homology, preferably 100% sequence homology to a DNA region flanking the target DNA sequence, and preferably flanking the preselected site in the genome of the plant cell;
    ii. A selectable or screenable marker gene located between the flanking DNA regions, the selectable or screenable marker gene further being located between one of the flanking DNA regions and a partial flanking DNA region, comprising part of the one of the flanking DNA regions, located in direct repeat;
    iii. A recognition site for a DSBI enzyme located between the one of the flanking DNA regions and the partial flanking DNA region located in direct repeat;
  c. Selecting a population of plant cells comprising the selectable or screenable marker;
  d. Selecting a plant cell wherein the DNA sequence of interest (and the selectable or screenable marker) has been introduced by homologous recombination through the flanking DNA regions, and regenerating a plant from the plant cell;
  e. Crossing the regenerated plant or a progeny plant thereof comprising the selectable marker gene with a plant comprising a rare cleaving double stranded break inducing ("DSBI") enzyme encoding chimeric gene, the chimeric gene comprising the following operably linked DNA segments:

i. a germline specific promoter fragment other than a promoter fragment selected from the nucleotide sequence of SEQ ID NO 3, such as a promoter fragment selected from the nucleotide sequence of SEQ ID No. 7;

ii. a DNA region encoding a double stranded DNA break inducing enzyme recognizing the recognition site located in the DNA of interest such as an endonuclease selected from the group of I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I or a chimeric endonuclease comprising a Zn finger DNA binding domain and a DNA cleavage domain;

iii. a transcription termination and polyadenylation region;

f. Selecting a progeny plant (F1-plant) comprising the selectable or screenable marker gene and the DSBI enzyme encoding chimeric gene;

g. Crossing the progeny plant with another plant;

h. Selecting a population of progeny plants (F2-population) which comprises the DSBI enzyme encoding chimeric gene; and i. Selecting a progeny plant wherein the selectable or screenable marker gene is deleted by homologous recombination between the one of the flanking DNA regions and a partial flanking DNA region comprising part of the one of the flanking DNA regions.

The invention also relates to the plants obtainable by the above described methods.

In yet another embodiment, the invention relates to a plant comprising a rare cleaving DSBI enzyme encoding chimeric gene, such as the chimeric gene of SEQ ID NO 6 from nucleotide 1941 to nucleotide 3913, the chimeric gene comprising the following operably linked DNA segments:

i. a germline specific promoter fragment other than a promoter fragment selected from the nucleotide sequence of SEQ ID NO 3, such as a promoter fragment selected from the nucleotide sequence of SEQ ID No. 7;

ii. a DNA region encoding a double stranded DNA break inducing enzyme recognizing the recognition site located in the DNA of interest, such as an endonuclease selected from the group of I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I or a chimeric endonuclease comprising a Zn finger DNA binding domain and a DNA cleavage domain, particularly the DNA region comprising the nucleotide sequence of SEQ ID No 1 or SEQ ID No 2; and iii. a transcription termination and polyadenylation region.

The invention also relates to the chimeric gene described above.

In another embodiment of the invention, a DNA vector is provided for exchanging a target DNA sequence in the genome of a plant cell for a DNA sequence of interest through the induction of a double stranded break at a preselected site within the target sequence or in the vicinity thereof, the DNA vector comprising a. the DNA sequence of interest located between two flanking DNA regions having at least 80% sequence homology, preferably a 100% sequence homology to a DNA region flanking the target DNA sequence and flanking the preselected site;

b. a selectable or screenable marker gene located between the flanking DNA regions, the selectable or screenable marker gene further being located between one of the flanking DNA regions and a partial flanking DNA region comprising part of the one of the flanking DNA regions located in direct repeat; and c. a recognition site for a DSBI enzyme located between the one of the flanking DNA regions and the partial flanking DNA region located in direct repeat.

In yet another embodiment of the invention a method for exchanging a target DNA sequence in the genome a plant for a DNA sequence of interest is provided comprising the following steps:

a) Inducing a first double stranded DNA break at a preselected site in the genome of the cell, the preselected site being located within the target DNA sequence or in the vicinity of said target DNA sequence;

b) Introducing a repair DNA molecule into the plant cell, whereby the repair DNA molecule comprises the following operably linked DNA fragments:

i. a DNA molecule having the nucleotide sequence of interest flanked at one side by a DNA region having at least 80% sequence homology, preferably 100% sequence homology to a DNA region in the vicinity of the target DNA sequence and of the preselected site in the genome of the plant cell;

ii. A selectable or screenable marker gene;

iii. At least one recognition site for a DSBI enzyme located in the vicinity of the selectable or screenable marker gene, preferably two recognition sites for a DSBI enzyme flanking the selectable or screenable marker gene;

c) Selecting a population of plant cells comprising the selectable or screenable marker;

d) Selecting a plant cell wherein the selectable or screenable marker has been introduced by homologous recombination through the flanking DNA region and by non-homologous end joining at the other side of the repair DNA and regenerating a plant from the plant cell;

e) Crossing the regenerated plant or a progeny plant thereof comprising the selectable marker gene with a plant comprising a DSBI enzyme encoding chimeric gene, the chimeric gene comprising the following operably linked DNA segments:

i. a germline-specific promoter;

ii. a DNA region encoding a double stranded DNA break inducing enzyme recognizing the recognition site located in the DNA of interest;

iii. a transcription termination and polyadenylation region;

f) Selecting a progeny plant (F1-plant) comprising the selectable or screenable marker gene and the DSBI enzyme encoding chimeric gene;

g) Crossing the progeny plant with another plant whereby the progeny plant is used as a pollen donor in case the germline specific promoter controls expression in the germline cells leading to pollen formation and wherein the progeny plant is used as female in case the germline specific promoter controls expression in the germline cells leading to ovules;
h) Selecting a population of progeny plants (F2-population) which comprises the DSBI enzyme encoding chimeric gene; and
i) Selecting a progeny plant within said F2 population wherein the selectable or screenable marker gene is deleted by intrachromosomal homologous recombination between the direct repeats generated by integration of the repair DNA, and wherein the target DNA sequence has been replaced by said DNA sequence of interest.

The invention also provides a method for introduction of a DNA molecule of interest into the genome of a plant cell or plant followed by removal of a subsequence of the DNA molecule of interest comprising the steps of
a. providing a plant comprising a DSBI enzyme encoding chimeric gene, the chimeric gene comprising the following operably linked DNA segments:
   i. a germline specific promoter;
   ii. a DNA region encoding a double stranded DNA break inducing enzyme recognizing the recognition site;
   iii. a transcription termination and polyadenylation region;
b. Introducing the DNA molecule of interest into the genome of the plant cell, whereby the DNA molecule of interest comprising the subsequence of the DNA molecule flanked by two DNA sequences arranged in direct repeat and further comprising at least one recognition site for a rare cleaving double stranded DNA break inducing (DSBI) enzyme located in the vicinity of, preferably between, the two DNA sequences arranged in direct repeat;
c. Selecting a plant cell wherein the DNA molecule of interest is integrated in the genome and regenerating a plant from the plant cell;
d. Crossing or selfing the regenerated plant
e. Selecting a progeny plant wherein subsequence of the DNA molecule has been deleted by homologous recombination between the two DNA sequences arranged in direct repeat; and optionally
f. Crossing the progeny plant wherein the subsequence of the DNA molecule has been deleted, with another plant; and
g. Obtaining a population of progeny plants (F3-plants) and selecting plants which do not contain the rare cleaving DSBI enzyme encoding chimeric gene.

Also provided is a method for exchanging a target DNA sequence in the genome of a plant for a DNA sequence of interest comprising the following steps:
a. Providing a plant comprising a DSBI enzyme encoding chimeric gene, the chimeric gene comprising the following operably linked DNA segments:
   i. a germline specific promoter other than a microspore specific promoter having the nucleotide sequence of SEQ ID No 3 from position 1-992;
   ii. a DNA region encoding a double stranded DNA break inducing enzyme recognizing the recognition site located in the DNA of interest;
   iii. a transcription termination and polyadenylation region;
b. Inducing a first double stranded DNA break at a preselected site in the genome of a cell of a plant, the preselected site being located within the target DNA sequence or in the vicinity of the target DNA sequence;
c. Introducing a repair DNA molecule of interest into the plant cell, the DNA molecule comprising
   i. The DNA sequence of interest located between two flanking DNA regions having at least 80% sequence homology to a DNA region flanking the target DNA sequence, and preferably flanking the preselected site in the genome of the plant cell;
   ii. A selectable or screenable marker gene located between the flanking DNA regions, the selectable or screenable marker gene further being located between one of the flanking DNA regions and another copy of at least part of the one of the flanking DNA regions located in direct repeat indicated as partial flanking DNA sequence;
   iii. At least one recognition site for a DSBI enzyme located between the one of the flanking DNA regions and the partial flanking DNA region located in direct repeat;
d. Selecting a population of plant cells comprising the selectable or screenable marker;
e. Selecting a plant cell wherein the selectable or screenable marker has been introduced by homologous recombination through the flanking DNA regions and regenerating a plant from the plant cell;
f. Crossing or selfing the plant;
g. Selecting a progeny plant wherein the selectable or screenable marker gene is deleted by homologous recombination between the one of the flanking DNA regions and a partial flanking DNA region comprising part of the one of the flanking DNA regions.

In yet another embodiment, the invention relates to a method for exchanging a target DNA sequence in the genome of a plant for a DNA sequence of interest comprising the following steps:
a) Providing a plant comprising a DSBI enzyme encoding chimeric gene, the chimeric gene comprising the following operably linked DNA segments:
   i) a germline-specific promoter;
   ii) a DNA region encoding a double stranded DNA break inducing enzyme recognizing the recognition site located in the DNA of interest;
   iii) a transcription termination and polyadenylation region;
b) Inducing a first double stranded DNA break at a preselected site in the genome of the cell, the preselected site being located within the target DNA sequence or in the vicinity of the target DNA sequence;
c) Introducing a repair DNA molecule into the plant cell, whereby the repair DNA molecule comprises the following operably linked DNA fragments:
   i) a DNA molecule having the nucleotide sequence of interest flanked at one side by a DNA region having at least 80% sequence homology, preferably 100% sequence homology to a DNA region in the vicinity of the target DNA sequence and of the preselected site in the genome of the plant cell;
   ii) A selectable or screenable marker gene;
   iii) At least one recognition site for a DSBI enzyme located in the vicinity of the selectable or screenable marker gene, preferably two recognition sites for a DSBI enzyme flanking the selectable or screenable marker gene;
d) Selecting a population of plant cells comprising the selectable or screenable marker;
e) Selecting a plant cell wherein the selectable or screenable marker has been introduced by homologous recombination through the flanking DNA region and by non-homologous end joining at the other side of the repair DNA and regenerating a plant from the plant cell;

f) Crossing or selfing the regenerated plant or a progeny plant thereof comprising the selectable marker gene; and g) Selecting a progeny plant within the F2 population wherein the selectable or screenable marker gene is deleted by intrachromosomal homologous recombination between the direct repeats generated by integration of the repair DNA, and wherein the target DNA sequence has been replaced by the DNA sequence of interest.

BRIEF DESCRIPTION OF THE DRAWINGS

FIG. 1 is schematic representation of a method for introducing a DNA of interest having a selected subpart comprising a selectable or screenable marker gene into a cell of a plant and subsequently removing the selected subpart of the DNA of interest.

Trait: represents any DNA sequence of interest; DSB: recognition site for a double stranded break inducing enzyme; DSBIE: region encoding a double stranded break inducing enzyme; SMG1: selectable marker gene or screenable marker gene; drs: direct repeat sequence; SMG2: selectable or screenable marker gene associated with the DSBIE encoding chimeric gene; GSP: germline specific promoter; 3': transcription termination and polyadenylation signal.

Figure 2A:
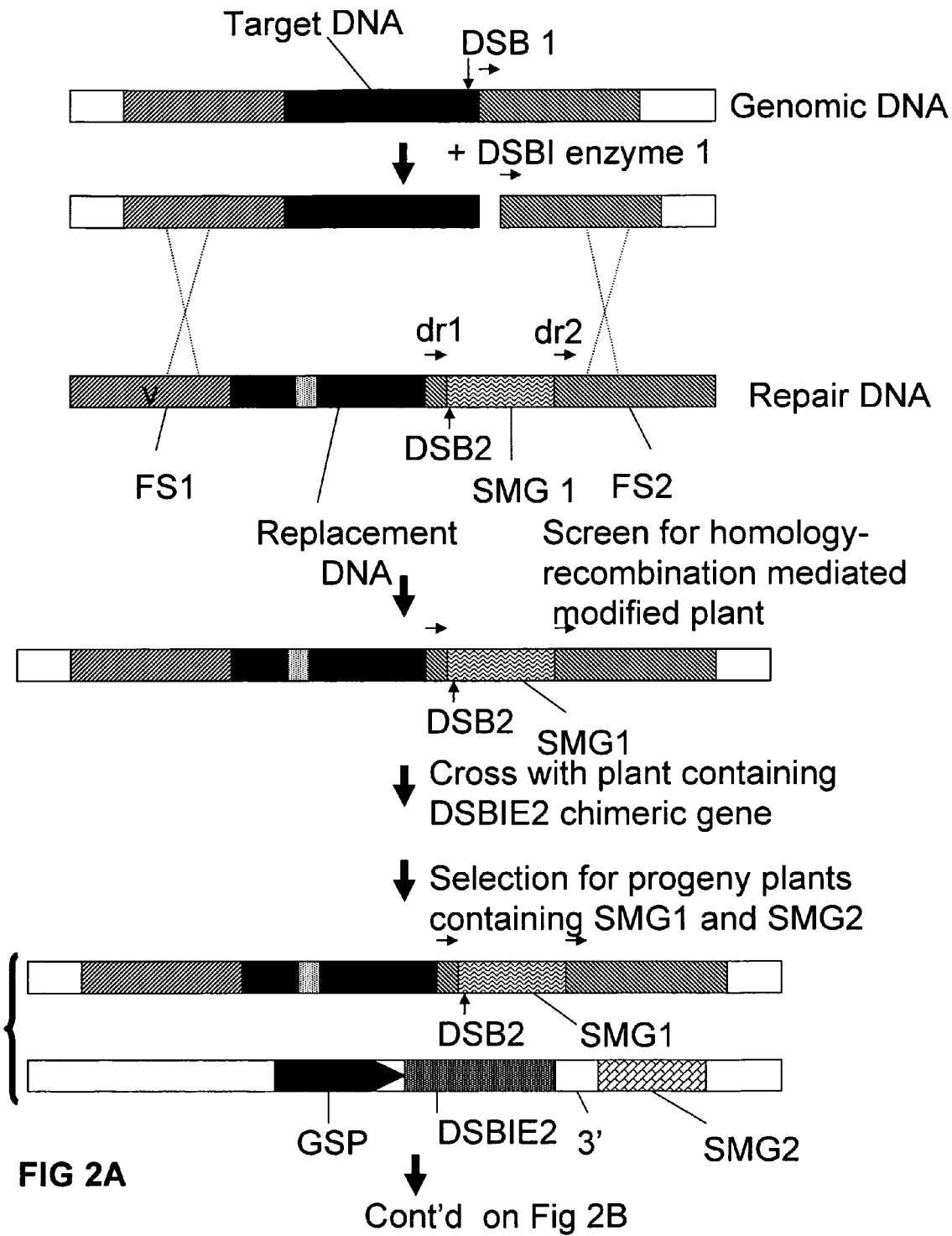
Figure 2B:
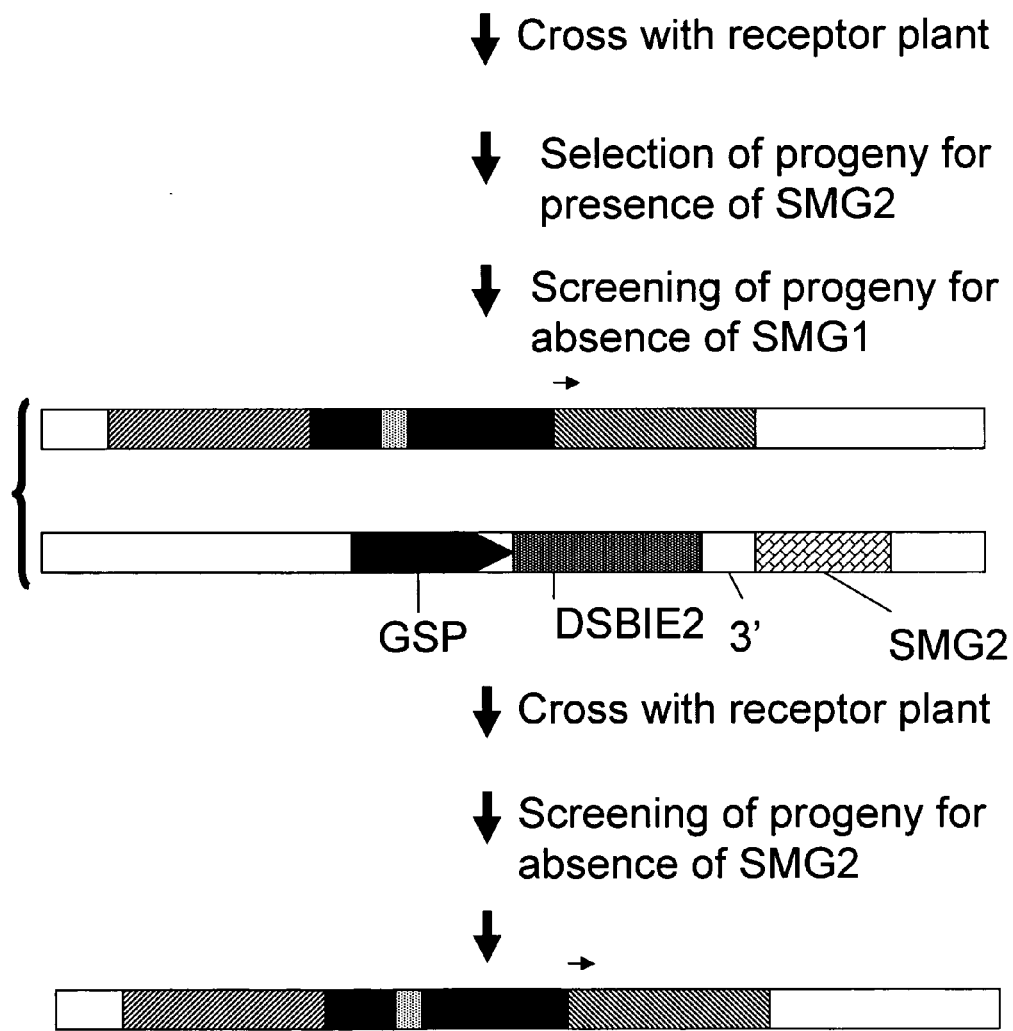

FIG. 2 is a schematic representation of a method allowing exact replacement of a target DNA sequence with a replacement DNA sequence. DSB1: recognition site for a first double stranded break inducing enzyme; FS1: flanking sequence 1; FS2: flanking sequence 2; DSB2: recognition site for a second double stranded break inducing enzyme; SMG1: selectable marker gene 1 or screenable marker gene 1; SMG2: selectable marker gene 2 or screenable marker gene 2; DSBIE: double stranded break inducing enzyme; dr1: direct repeat sequence 1 (which is similar or identical to the direct repeat sequence 2 that is part of flanking sequence 2; also indicated herein as "partial flanking DNA region"); GSP: germline specific promoter; 3': transcription termination and polyadenylation signal.

Figure 3A:
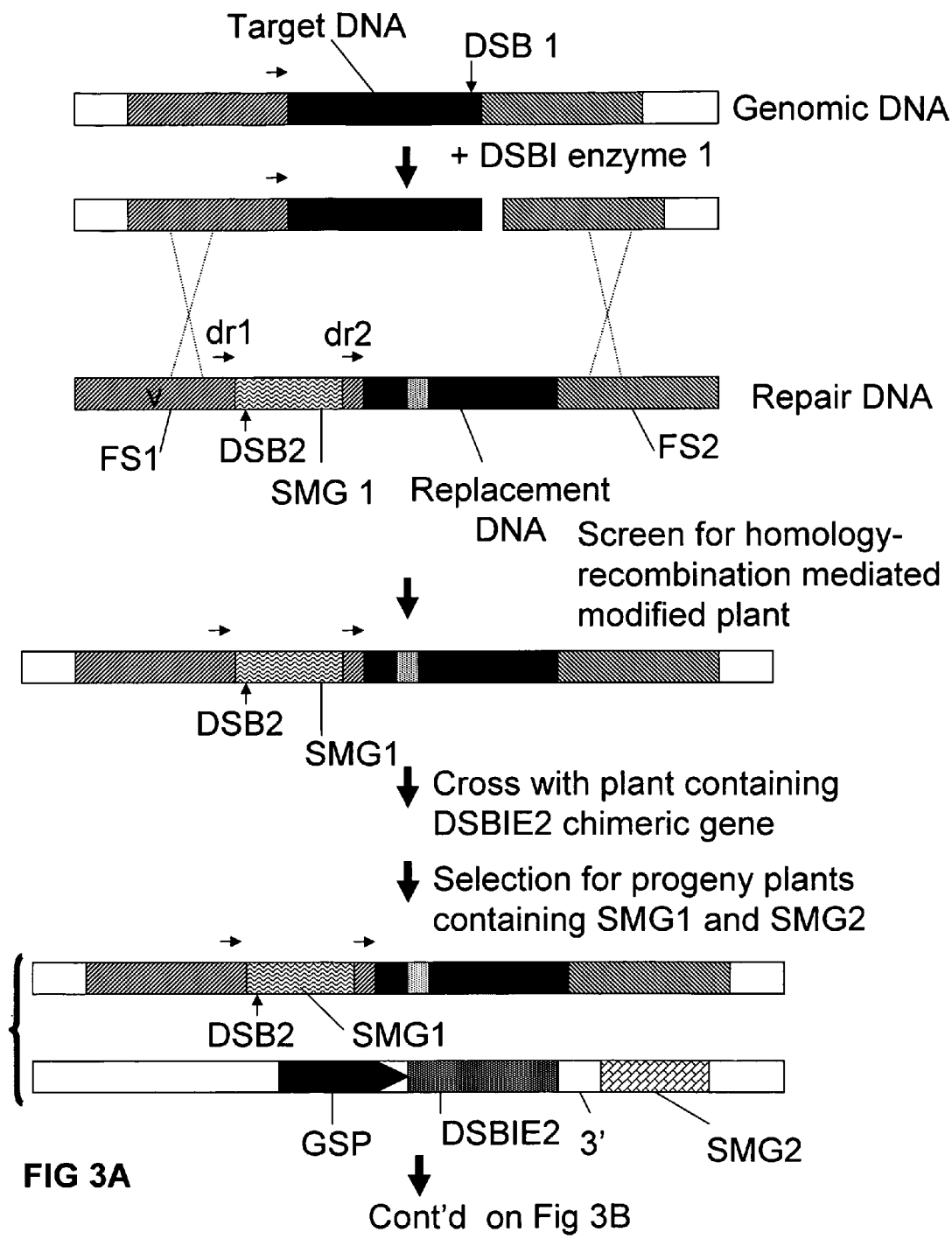
Figure 3B:
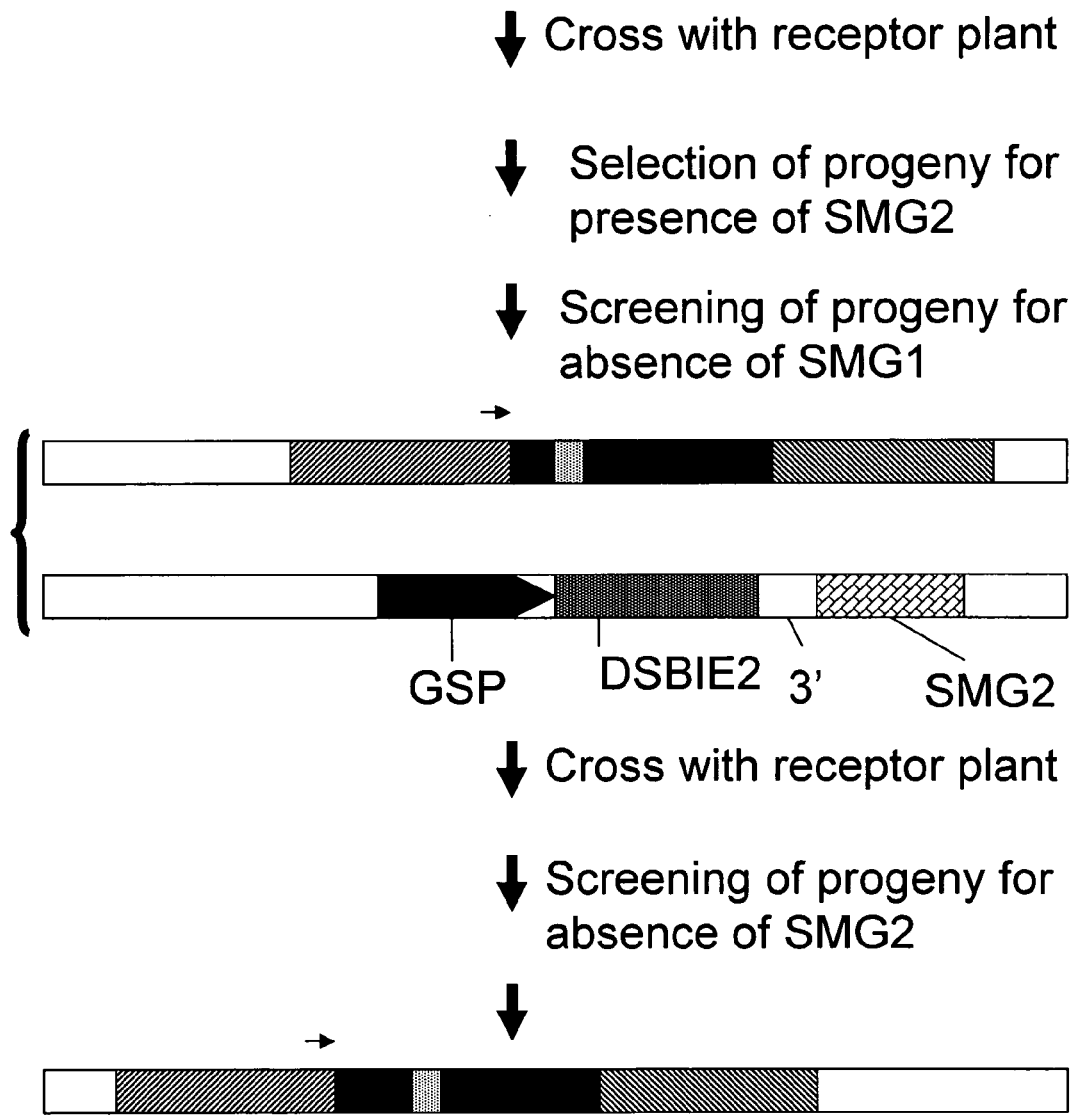

FIG. 3 is a schematic representation of a method allowing exact replacement of a target DNA sequence with a replacement DNA sequence similar to the method illustrated in FIG. 2. dr1 in this case is a direct repeat sequence which is part from flanking sequence 1 and which is similar or identical to the direct repeat sequence 2 (dr2). Abbreviations are as used in the other figures.

Figure 4A:
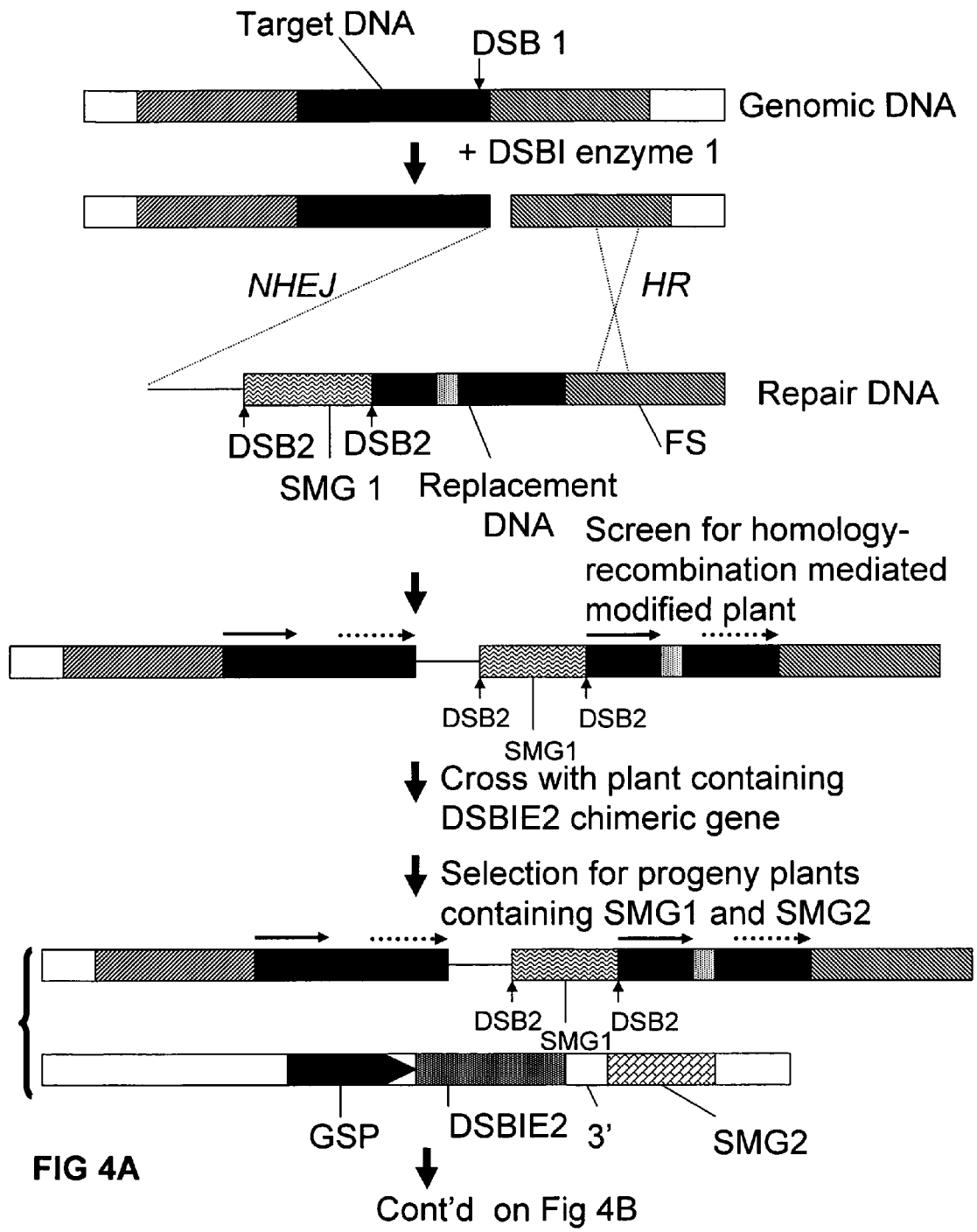
Figure 4B:
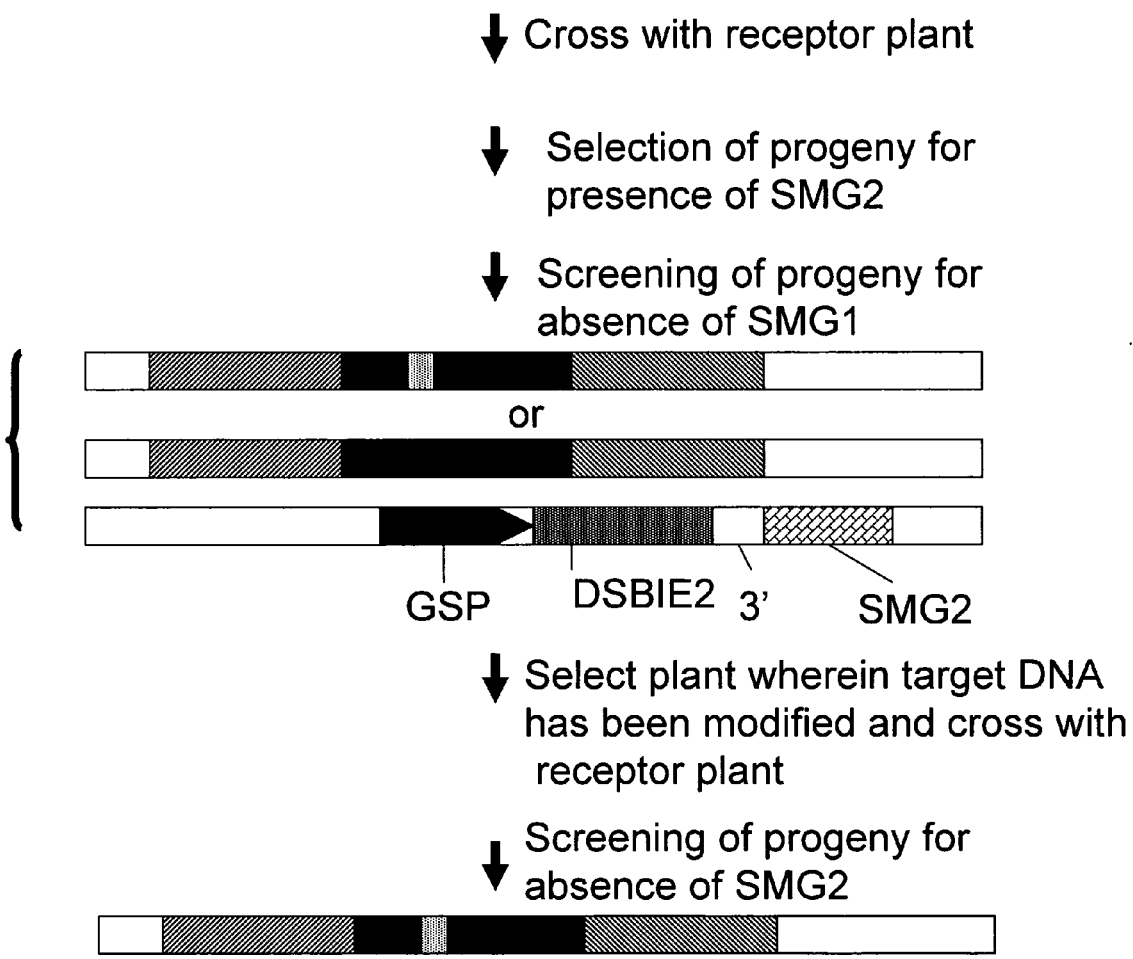

FIG. 4 is a schematic representation of a method allowing exact replacement of a target DNA sequence whereby only one flanking DNA sequence is used. HR: homologous recombination; NHEJ: non-homologous end-joining; FS: flanking DNA sequence. In this non-limitative embodiment two recognition sites are used for DSBIE2. Two sets of direct repeats are generated during the recombination/integration and are indicated by arrows (either full or dashed). Other abbreviations are as used in the other figures.

DETAILED EMBODIMENTS OF THE INVENTION

The current invention is based on the finding that selected sequences of a DNA molecule which are flanked by two direct repeats, and which are located in the neighborhood of a recognition site for a rare-cleaving double stranded DNA break inducing enzyme can be efficiently removed when the plant comprising such DNA is first crossed with a plant comprising a chimeric gene encoding the double stranded DNA break inducing rare-cleaving enzyme under control of a germline-selective or germline-specific promoter, such as a microspore-specific promoter (e.g. NTM19) or a promoter which is expressed in the megaspore (e.g. BnSKP1γ1), and using the gametes of the resulting plant in further breeding.

Figure 1A:
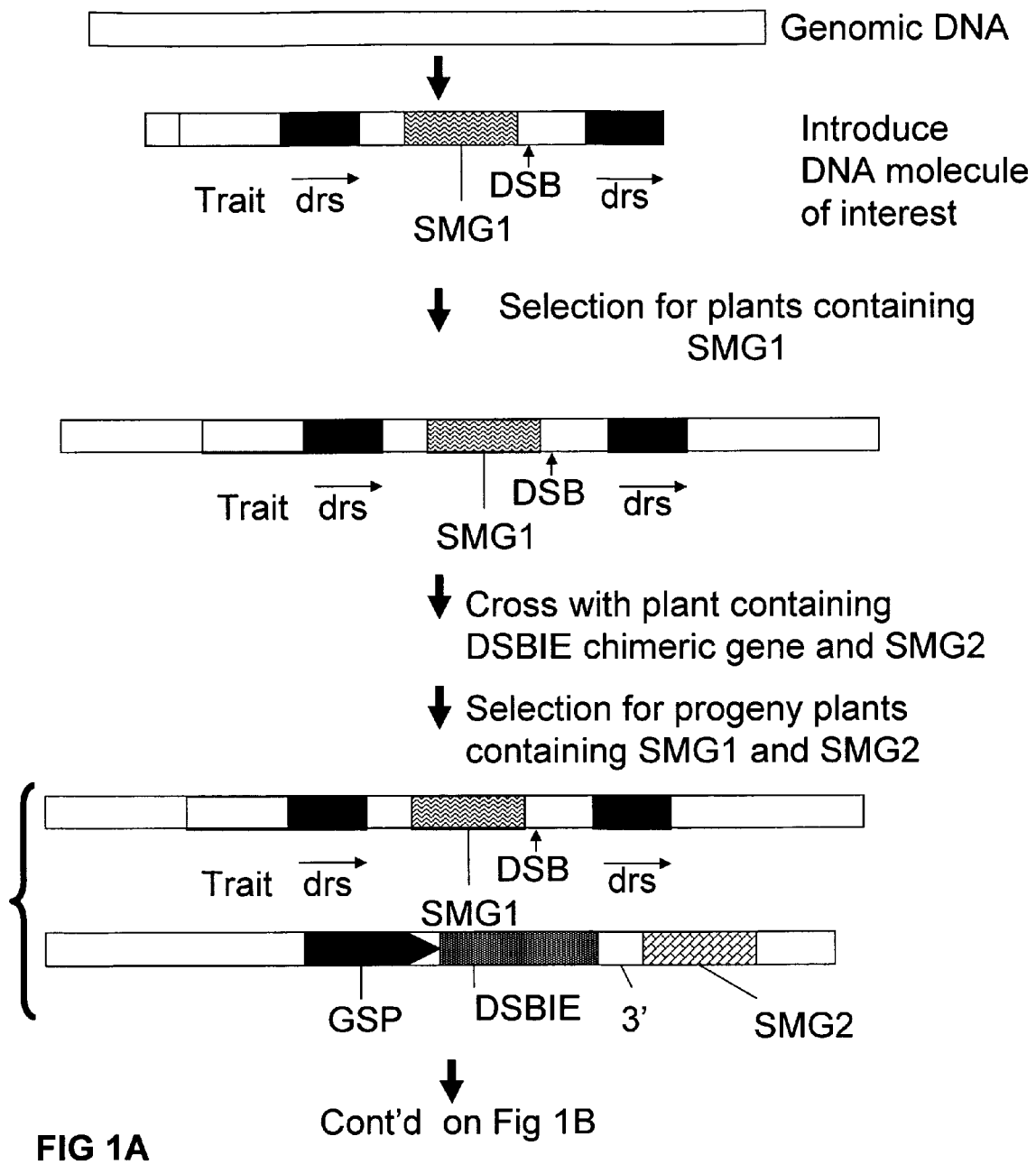
FIGS. 1 to 4 represent different embodiments of the method to remove a selected subpart of a DNA of interest which is or has been introduced into a cell of a plant. They are for illustration purposes only and should not be used to construe the claims in a limiting manner.

Thus, the invention is in one embodiment directed towards the use of plant comprising a chimeric gene encoding a double stranded DNA break inducing rare-cleaving endonuclease under control of a germline specific promoter, other than the promoter region of the NTM19 gene from tobacco, to remove, by crossing, a DNA fragment located in the vicinity of a recognition site for the double stranded DNA break inducing rare-cleaving endonuclease and further located between two sequences located in direct repeat orientation (see FIG. 1 wherein a micro-spore specific promoter is used). The expression of the rare cleaving DSBI endonuclease in the microspore during the gamete formation is sufficient to induce double stranded DNA breaks and thereby significantly stimulates the intrachromosomal homologous recombination between the directly repeated sequences, resulting in a removal of the sequences located between these directly repeated sequences.

In other words, in one embodiment of the invention, a method for introduction of a DNA molecule of interest into the genome of a plant cell or plant followed by removal of a subsequence of that DNA molecule is provided comprising the steps of a. Introducing that DNA molecule of interest into the genome of the plant cell comprising the subsequence of that DNA molecule flanked by two DNA sequences arranged in direct repeat and further comprising at least one recognition site for a double stranded DNA break inducing (DSBI) rare cleaving endonuclease located between the two DNA sequences arranged in direct repeat;

b. Selecting a plant cell wherein the DNA molecule of interest is integrated in the genome and regenerating a plant from the plant cell;

c. Crossing the plant with a second plant comprising a DSBI enzyme encoding chimeric gene, the chimeric gene comprising the following operably linked DNA segments:
  i. a germline-selective or germline-specific promoter other than the promoter region of the NTM 19 gene from tobacco;
  ii. a DNA region encoding a rare cleaving double stranded DNA break inducing enzyme recognizing the recognition site;
  iii. a transcription termination and polyadenylation region;

d. Selecting a progeny plant (F1-plant) comprising the DNA molecule of interest and the DSBI enzyme encoding chimeric gene;

e. Crossing the progeny plant with another plant whereby the progeny plant (F1-plant) is used as pollen donor or as female receptacle plant;

f. Selecting a population of progeny plants (F2-population) which comprises the DSBI enzyme encoding chimeric gene; and g. Selecting a progeny plant wherein the subsequence of the DNA molecule of interest has been deleted by homologous recombination between the two DNA sequences arranged in direct repeat.

As used herein, a "double stranded DNA break inducing rare-cleaving endonuclease" is an enzyme capable of inducing a double stranded DNA break at a particular nucleotide sequence, called the "recognition site". Rare-cleaving endonucleases, also sometimes called mega-nucleases have a recognition site of 14 to 40 consecutive nucleotides. Therefore, rare-cleaving endonucleases have a very low frequency of cleaving, even in the larger plant genomes. Homing endonucleases constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level.

A well characterized homing endonuclease is I-SceI. I-SceI is a site-specific endonuclease, responsible for intron mobility in mitochondria in *Saccharomyces cerevisea*. The enzyme is encoded by the optional intron Sc LSU.1 of the 21S rRNA gene and initiates a double stranded DNA break at the intron insertion site generating a 4 bp staggered cut with 3'OH overhangs. The recognition site of I-SceI endonuclease extends over an 18 bp non-symmetrical sequence (Colleaux et al. (1988) Proc. Natl. Acad. Sci. USA 85: 6022-6026). The amino acid sequence for I-SceI and a universal code equivalent of the mitochondrial I-SceI gene have been provided by e.g. WO96/14408. WO96/14408 further discloses a number of variants of I-SceI protein which are still functional.

PCT application WO05/049842 (incorporated herein by reference) provides synthetic nucleotide sequence variants of I-SceI which have been optimized for expression in plants. The nucleotide sequence of such synthetic I-Sce I coding regions is set forth in SEQ ID No 1 in UIPAC code. The symbols of the UIPAC code have their usual meaning i.e. N=A or C or G or T; R=A or G; Y=C or T; B=C or G or T (not A); V=A or C or G (not T); D=A or G or T (not C); H=A or C or T (not G); K=G or T; M=A or C; S=G or C; W=A or T.

A list of other rare cleaving DSB inducing enzymes and their respective recognition sites is provided in Table I of WO03/004659 (pages 17 to 20) (incorporated herein by reference). These include I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-Dhal, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I.

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO03/080809, WO94/18313 or WO95/09233 and in Isalan et al. (Nature Biotechnology (2001) 19: 656-660) or Liu et al. (Proc. Natl. Acad. Sci. USA (1997) 94: 5525-5530). Another way of producing custom-made meganucleases, by selection from a library of variants, is described in WO04/067736.

As used herein "flanked by two DNA sequences arranged in direct repeat" indicates that the sequence to be removed from the introduced DNA molecule is immediately preceded and followed by two DNA regions, one at each end, wherein the two DNA regions are essentially similar in nucleotide sequence. The directly repeated sequences need not be identical, but may vary between about 75% to about 100% sequence identity. The shorter the repeated sequence, the more stringent the requirement for sequence similarity preferably is. However, in order to restore the DNA sequence without leaving a footprint, as described hereinafter, the DNA sequences arranged in direct repeat should preferably be identical. For avoidance of doubt, if the two DNA regions essentially similar in nucleotide sequence are contained within a double stranded DNA molecule, these DNA sequences are to be located on the same DNA strand, in the same 5'→3' direction.

The repeated DNA sequence may be at least 10, 20, 50 or 100 nucleotides in length, but the sequence may of course be larger. It has however been found that repeats longer than 300 nucleotides do not any longer significantly enhance the intra-chromosomal homology recombination resulting in the removal of the DNA sequence located between the direct repeat sequences.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch (1970) J. Mol. Biol. 48(3): 443-53).) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Although the DSBI recognition site is preferably located between the directly repeated DNA sequences, this is not essential nor required. Indeed, the DSBI recognition site could also be part of one of the repeated DNA sequences.

As used herein "located in the vicinity" refers to the DSBI being located at a distance of between 500 bp, 1 kbp to 10 kbp from the directly repeated DNA sequences.

As described herein, the DNA molecule of interest comprises at least one recognition site for a rare cleaving DSBI enzyme located in the vicinity of the two DNA sequences arranged in direct repeat. Accordingly, the DNA molecule of interest may comprise two recognition sites for a rare cleaving DSBI enzyme which may be located each in the vicinity of one of the flanking direct DNA repeats.

The methods herein described require the use of a chimeric gene encoding a rare-cleaving double stranded break inducing enzyme, whereby the coding region for the endonuclease is under control of a germline specific promoter fragment, preferably a gametophyte specific promoter fragment.

As used herein, a "germline-specific promoter" is a promoter region, promoter or fragment which can promote transcription selectively, preferably specifically in plant cells that ultimately produce the gametes starting from megaspore-mother cell or the meiocyte. A germline-specific promoters as defined herein thus include gametophyte-specific promoter, gamete-specific promoters, promoters which control expression in microspores and/or megaspores or in their respective immediate precursor cells.

As used herein, a "promoter specific for gametogenesis" is a promoter region, promoter or fragment which can promote transcription selectively, preferably specifically in plant cells which are the immediate precursor cells of the gametes.

In angiosperm plants, sexual reproduction requires the production of viable male and female gametophytes. Pollen, as the male gametophyte is formed within the anther and is initiated from sporogenous cells, which develop into meiocytes. The meiocyte undergoes meiosis to form a tetrad of haploid microspores, which are subsequently released into the anther locule. Following expansion and vacuolation, an asymmetrical mitosis of the microspore results in bicellular pollen, containing a vegetative and a generative cell. In the majority of species, pollen is shed in bicellular condition. The female gametophyte, the embryo sac, initiates in the ovary from the megaspore mother cell or megasporocyte through two meiotic divisions, resulting in the formation of a linear tetrad of haploid megaspores. The chalazal megaspore enlarges in the preparation for the first mitotic division in the female gametophyte development, while the other three megaspores degenerate. Mitotic divisions occur in three generations of nuclei so that an eight nucleate embryo sac is formed. During these divisions the former megaspore cell enlarges and becomes much vacuolated. The eight-nucleate cell is organized into the seven-celled embryo sac through the delimitation by cell walls of six of the nuclei and associated cytoplasm. The three cells at the micropylar end constitute the egg apparatus which is composed of the egg and two synergids. At the opposite end of the embryo sac are three antipodal cells. Between the two groups of cells is the large central cell containing two polar nuclei, which may fuse prior to fertilization and form the diploid secondary endosperm nucleus.

As used herein "a microspore specific promoter region" or "a microspore specific promoter" or "a microspore specific promoter fragment" is a promoter region or promoter or promoter fragment which can promote transcription selectively, preferably specifically, in the unicellular microspore of a plant. A suitable microspore specific promoter region is described in WO97/30166 (incorporated herein by reference; see also SEQ ID No 3) as the promoter region from NTM19 gene in tobacco. A functional fragment thereof has been incorporated in the chimeric gene of the Examples (SEQ ID No 6). A microspore specific promoter fragment could include the nucleotide sequence of SEQ ID No 3 from position I to position 954 or from position 1 to position 993 or the nucleotide sequence of SEQ ID No 6 from position 1941 to 2926.

As used herein "a megaspore specific promoter region" or "a megaspore specific promoter" or "a megaspore specific promoter fragment" is a promoter region or promoter or promoter fragment which can promote transcription selectively, preferably specifically, in a unicellular megaspore of a plant, preferably a megaspore which develops into an embryo sac.

Particular promoters such as the BnSKP1γ1 (SEQ ID NO 7) may control transcription specifically or selectively both in microspores and megaspores of plants (Drouad et al. Sex Plant Reprod. (2000) 13: 29-35).

Suitable germline-specific promoters may be any one of the following (citations below are herein incorporated by reference):

i. A promoter comprising an *Arabidopsis* egg apparatus (EA) specific enhancer, fused to a minimal promoter element such as a minimal 35S promoter, as described by Yang et al. (Plant Physiol. (2005) 139(3): 1421-1432)

ii. An *Arabidopsis* TAG1 promoter as described by Galli et al. (Genetics (2003) 165(4): 2093-2105) (expressed in male and female gametophytes)

iii. An *Arabidopsis* Duo1 promoter (male generative cell and sperm cell activity as described by Rotman et al. (Curr Biol. (2005) 15(3): 244-248)

iv. promoters as could be isolated from the female gametophytic genes described by Yu et al. (Plant Physiology (2005) 139(4): 1853-1869)

v. a promoter from LGC1 from *Lilium* expressed in male generative cell and sperm cells (Xu et al. (1999) Proc Natl Acad Sci USA 96(5): 2554-2558; Singh et al. (2003) FEBS Lett. 542(1-3): 47-52).

vi. A promoter from the ERCC1 homolog expressed in male sperm cells (Xu et al. (1998) Plant J. 13(6): 823-829)

vii. A promoter from H2A or H3 histone genes (Xu et al. (1999) Plant Mol. Biol. 39: 607-614; Okada et al. (2005) Plant Cell Physiol. 46: 797-802)

viii. Promoters from sperm cell genes as identified in rice (Chen, Schuan University, GenBank entries BE225314 to BE225323, BF475189 to BF475237) and as identified in corn (Engel et al. (2003) Plant J. 34: 697-707)

ix. The Zmea1 promoter (Marton et al. (2005) Science 307: 573-576) and Zmes promoters (Cordts et al. (2001) Plant J. 25(1): 103-114) specific for egg apparatus and embryosac, respectively x. Promoters comprising silencer elements recognized by GRSF or germline restrictive silencing factor (Haerizadeh et al. (2006) Science 28(313): 496-499)

xi. BNM1 or BnM3.4 promoter described by Guerche et al. (Plant Mol. Biol. (1999) 40: 857-872) and promoters driving expression of microspore-specific cDNAs M21.

Having read through the current specification, the person skilled in the art will realize that promoters which are expressed specifically or selectively in the plant gametes such as pollen specific promoter regions or egg apparatus specific promoter regions are also suitable promoters to achieve similar results.

WO06/105946 has disclosed one particular microspore specific promoter from the tobacco gene NTM19 (SEQ ID NO 3). To the extent that the claimed methods herein described are identical (other than in the use of germline specific promoter) a germline specific promoter could be interpreted as a germline specific promoter other than a promoter having the nucleotide sequence of SEQ ID NO 3 from nucleotide 1 to 992 or the nucleotide sequence of SEQ ID NO 6 from nucleotide 1941 to nucleotide 2926, or a germline specific promoter other than a microspore specific promoter from the tobacco gene NTM 19 or germline-specific promoter other than a microspore specific promoter.

As used herein "coding region for a rare cleaving double stranded break inducing endonuclease" or "coding region for a rare cleaving double stranded break inducing enzyme" is a nucleotide sequence which encodes a polypeptide that is characterized as a rare cleaving DSBI enzyme such as the homing endonucleases or the chimeric endonucleases described elsewhere in this application. The coding region may thus comprise any nucleotide sequence that encodes any of the amino acid sequences of the homing endonucleases listed in the following table, which can be found in public databases under the mentioned accession numbers (all herein incorporated by reference):

| DSBI enzyme | Accession number |
| --- | --- |
| I-AniI | P03880 |
| I-CvuI | P56347 |
| I-CreI | P05725 |
| I-ChuI | Q32001 |
| I-CpaI - I-CpaIII - I-CpaIV - I-CpaV | Q39562/Q8WKZ5/Q8WKZ6/Q8WKZ8 |
| I-CpaII | Q39559 |
| I-CeuI | P32761 |
| I-DmoI | P21505 |
| I-SceI | P03882 |
| I-SceII | P03878 |
| I-SceIII | Q9ZZX3 |
| PI-SceI | P17255 |
| I-NanI | Q25535 |
| I-NitI | Q25567 |
| I-NjaI | Q25568 |
| I-PpoI | Q94702 |
| PI-PfuI | O73954 |
| PI-PkoI | P77933 |
| PI-PkoII | P77933 |
| PI-PspI | Q51334 |
| PI-TfuI | P74918 |
| PI-TfuII | P74918 |
| PI-ThyI | Q9HH05 |
| PI-ThyII | Q9HH05 |
| PI-TliI | P30317 |
| PI-TliII | P30317 |
| I-TevI | P13299 |
| I-TevII | P07072 |
| I-TevIII | Q38419 |

It will be clear that for expression of the endonucleases under the control of a germline specific promoter fragment, the coding region should be adapted so that the universal codon language is used to encode the above mentioned polypeptides. The coding region may further be optimized for expression in plants and the synthetic coding region has a nucleotide sequence which has been designed to fulfill the following criteria:
  a) the nucleotide sequence encodes a functional rare cleaving double stranded break inducing endonuclease,
  b) the nucleotide sequence has a GC content of about 50% to about 60%
  c) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;
  d) the nucleotide sequence does not comprise a nucleotide sequence selected from the group consisting of CCAAT, ATTGG, GCAAT and ATTGC;
  e) the nucleotide sequence does not comprise a sequence selected from the group consisting of ATTTA, AAGGT, AGGTA, GGTA or GCAGG;
  f) the nucleotide sequence does not comprise a GC stretch consisting of 7 consecutive nucleotides selected from the group of G or C;
  g) the nucleotide sequence does not comprise a GC stretch consisting of 5 consecutive nucleotides selected from the group of A or T; and
  h) the nucleotide sequence does not comprise codons coding for Leu, Ile, Val, Ser, Pro, Thr, Ala that comprise TA or CG duplets in positions 2 and 3 (i.e. the nucleotide sequence does not comprise the codons TTA, CTA, ATA, GTA, TCG, CCG, ACG and GCG).

The double stranded break inducing enzyme may comprise, but need not comprise, a nuclear localization signal (NLS) (Raikhel (1992) Plant Physiol 100: 1627-1632 and references therein), such as the NLS of SV40 large T-antigen (Kalderon et al. (1984) Cell 39: 499-509). The nuclear localization signal may be located anywhere in the protein, but is conveniently located at the N-terminal end of the protein. The nuclear localization signal may replace one or more of the amino acids of the double stranded break inducing enzyme.

Although the methods for removal are herein described as involving an active step of introduction of a DNA molecule of interest, followed by removal of selected subfragment thereof, it will be clear that the removal method of the invention can be used to remove any sequence located between direct DNA repeats, provided that a DSBI enzyme can be found or engineered that recognizes a DSBI recognition site in the vicinity of the repeated DNA sequences.

It will also be clear that the terms used to describe the method such as "introduction of a DNA fragment" as well as "regeneration of a plant from the cell" do not imply that such DNA fragment necessarily needs to be introduced by transformation techniques. Indeed, it will be immediately clear to the person skilled in the art that the DNA molecule of interest may also be introduced by breeding or crossing techniques from one plant to another.

However, it will be clear that the DNA molecule of interest may be introduced into the plant cells by any method known in the art, including *Agrobacterium* mediated transformation but also by direct DNA transfer methods. The transforming DNA molecule can be transferred into plant cells using any conventional method, including but not limited to direct DNA transfer method. As used herein "direct DNA transfer" is any method of DNA introduction into plant cells which does not involve the use of natural *Agrobacterium* spp. and which is capable of introducing DNA into plant cells. This includes methods well known in the art such as introduction of DNA by electroporation into protoplasts, introduction of DNA by electroporation into intact plant cells or partially degraded tissues or plant cells, introduction of DNA through the action of agents such as PEG and the like, into protoplasts, use of silicon whiskers, and bombardment with DNA coated microprojectiles.

The DNA may be integrated by homologous recombination or non-homologous end-joining methods involving a double stranded break induction at a preselected site as described e.g. in WO05/049842.

In one particular embodiment of the invention, the method of removal may be used in combination with DNA insertion, deletion or replacement by targeted homologous recombination, and wherein the targeted DNA insertion is accompanied by the initial integration of a selectable or screenable marker, followed by verification in the population of plant cells or plants comprising the selectable or screenable marker of those plant cells or plants wherein the targeted DNA insertion occurred by homologous recombination. When the flanking sequences and direct repeats are appropriately chosen, this method results in exact replacement of the target DNA for a DNA of interest, without any remainder ("footprint") of the DNA molecule of interest used to achieve the replacement. The method of removal further does not need any additional in vitro culture, thereby avoiding that somaclonal variations are generated. A schematical outline of the method can be found in FIGS. 2 and 3.

Interestingly, it has been observed that using the methods as described in WO05/049842 for targeted insertion of foreign DNA of interest through homologous recombination, those transformation events wherein the foreign DNA is indeed inserted through homologous recombination represent a relatively high proportion (in the order of 1 to 5%) of the total population of events wherein the DNA is incorporated in the plant chromosome by any means. Accordingly, there is no need to rely on the generation or recreation through the homologous recombination of a DNA sequence resulting in a recognizable phenotype (such as the creation of an intact selectable marker gene after homologous recombination) to identify those events whereby the DNA is inserted by homologous recombination. Rather, a selectable or screenable marker gene can be included in the DNA region between the flanking DNA sequences followed by analysis of a relatively small number of transformed plant cells or plants, for identification of those transformation events wherein targeted DNA insertion occurred through homologous recombination.

Thus, in this embodiment of the invention, a method is provided for exchanging a target DNA sequence in cells of a plant for a DNA sequence of interest (or a foreign DNA) comprising the following steps:

Inducing a first double stranded DNA break at a preselected site in the genome of the cell, the preselected site being located within the target DNA sequence or in the vicinity of the target DNA sequence;

Introducing a repair DNA molecule into the plant cell, whereby the repair DNA molecule comprises the following operably linked DNA fragments:
  i. a DNA molecule of interest located between two flanking DNA regions having at least 80% sequence homology, preferably 100% sequence homology to a DNA region flanking the target DNA sequence and flanking the preselected site in the genome of the plant cell;
  ii. A selectable or screenable marker gene located between the flanking DNA regions, whereby the selectable or screenable marker gene is further located between one of the flanking DNA regions and another copy of at least part of the mentioned one of the flanking DNA regions located in direct repeat (also indicated as partial flanking DNA sequence);
  iii. At least one recognition site for a DSBI enzyme located between the one of the flanking DNA regions and the partial flanking DNA region located in direct repeat;

Selecting a population of plant cells comprising the selectable or screenable marker;

Selecting a plant cell wherein the selectable or screenable marker has been introduced by homologous recombination through the flanking DNA regions and regenerating a plant from the plant cell;

Crossing the regenerated plant or a progeny plant thereof comprising the selectable marker gene with a plant comprising a DSBI enzyme encoding chimeric gene, the chimeric gene comprising the following operably linked DNA segments:
  i. a germline-specific promoter other than the promoter region of the NTM 19 gene from tobacco;
  ii. a DNA region encoding a double stranded DNA break inducing enzyme recognizing the recognition site located in the DNA of interest;
  iii. a transcription termination and polyadenylation region;

Selecting a progeny plant (F1-plant) comprising the selectable or screenable marker gene and the DSBI enzyme encoding chimeric gene;

Crossing the progeny plant with another plant whereby the progeny plant is used as a pollen donor in case the germline specific promoter controls expression in the germline cells leading to pollen formation and wherein the progeny plant is used as female in case the germline specific promoter controls expression in the germline cells leading to ovules;

Selecting a population of progeny plants (F2-population) which comprises the DSBI enzyme encoding chimeric gene; and Selecting a progeny plant within the F2 population wherein the selectable or screenable marker gene is deleted by homologous recombination between the one of the flanking DNA regions and a partial flanking DNA region comprising part of the one of the flanking DNA regions.

Thus, as used herein "a preselected site" indicates a particular nucleotide sequence in the plant nuclear genome, located in or near the target DNA sequence at which location it is desired to insert the foreign DNA or to exchange the target DNA sequence. A person skilled in the art would be able to either choose a double stranded DNA break inducing ("DSBI") enzyme recognizing the selected target nucleotide sequence or engineer such a DSBI endonuclease. Alternatively, a DSBI endonuclease recognition site may be introduced into the plant genome using any conventional transformation method or by conventional breeding using a plant line having a DSBI endonuclease recognition site in its genome, and any desired foreign DNA may afterwards be introduced into that previously introduced preselected target site.

The double stranded DNA breaks in the transforming DNA molecule may be induced conveniently by transient introduction of a plant-expressible chimeric gene comprising a plant-expressible promoter region operably linked to a DNA region encoding a double stranded break inducing enzyme. The DNA region encoding a double stranded break inducing enzyme may be a synthetic DNA region, such as but not limited to, a synthetic DNA region whereby the codons are chosen according to the design scheme as described elsewhere in this application for I-SceI encoding regions. The endonuclease itself, as a protein, could also be introduced into the plant cells, e.g. by electroporation. However, the endonuclease can also be provided in a transient manner by introducing into the genome of a plant cell or plant, a chimeric gene comprising the endonuclease coding region operably linked to an inducible plant-expressible promoter, and providing the appropriate inducible compound for a limited time prior to, during or immediately after introduction of the transforming DNA molecule. The endonuclease could also be provided as an RNA precursor encoding the endonuclease.

The double stranded break inducing enzyme may comprise, but need not comprise, a nuclear localization signal (NLS) (Raikhel (1992) Plant Physiol 100: 1627-1632, and references therein), such as the NLS of SV40 large T-antigen [Kalderon et al. (1984) Cell 39: 499-509). The nuclear localization signal may be located anywhere in the protein, but is conveniently located at the N-terminal end of the protein. The nuclear localization signal may replace one or more of the amino acids of the double stranded break inducing enzyme.

As used herein, the "target DNA sequence" is the DNA sequence located in the genome of the plant cell which is modified, by addition, deletion or substitution.

As used herein "flanking DNA regions" are DNA sequences having homology to the DNA regions respectively upstream or downstream of the target DNA sequence. This allows to better control the insertion of the foreign DNA or the DNA molecule of interest. Indeed, integration by homologous recombination will allow precise joining of the foreign DNA fragment to the plant nuclear genome up to the nucleotide level.

The flanking DNA regions may vary in length, and should be at least about 10 nucleotides in length. However, the flanking region may be as long as is practically possible (e.g. up to about 100-150 kb such as complete bacterial artificial chromosomes (BACs)). Preferably, the flanking region will be about 50 bp to about 2000 bp. Moreover, the regions flanking the foreign DNA of interest need not be identical to the DNA regions flanking the preselected site and may have between about 80% to about 100% sequence identity, preferably about 95% to about 100% sequence identity with the DNA regions flanking the preselected site. The longer the flanking region, the less stringent the requirement for homology. Furthermore, it is preferred that the sequence identity is as high as practically possible in the vicinity of the location of exact insertion of the foreign DNA. Furthermore, to achieve exchange of the target DNA sequence without changing the DNA sequence of the adjacent DNA sequences, the flanking DNA sequences should preferably be identical to the DNA regions flanking the preselected site.

Moreover, the regions flanking the foreign DNA of interest need not have homology to the regions immediately flanking the preselected site, but may have homology to a DNA region of the nuclear genome further remote from that preselected site. Insertion of the foreign DNA will then result in a removal of the target DNA between the preselected insertion site and the DNA region of homology. In other words, the target DNA located between the homology regions will be substituted for the foreign DNA of interest.

Preferably, the preselected site and the further mentioned recognition sequence are recognized by different rare cleaving double stranded break inducing endonucleases.

The mentioned "partial flanking DNA region" indicates that the DNA region comprises at least a portion of the flanking DNA region adjacent to DNA region to be deleted and which usually will comprise the selectable or screenable marker. It is clear that the partial flanking DNA sequence may also be equal in length to the flanking DNA sequence or even comprise a longer flanking DNA sequence.

"Selectable or screenable markers" as used herein have there usual meaning in the art and include, but are not limited to plant expressible phosphinotricin acetyltransferase, neomycine phosphotransferase, glyphosate oxidase, glyphosate tolerant EPSP enzyme, nitrilase gene, mutant acetolactate synthase or acetohydroxyacid synthase gene, β-glucoronidase (GUS), R-locus genes, green fluorescent protein and the likes. The selectable or screenable marker may also be a marker allowing both positive and negative selection, depending on the circumstances, as described e.g. in WO04/013333 or WO05/090581.

The selection of the plant cell or plant wherein the selectable or screenable marker and the rest of the foreign DNA molecule has been introduced by homologous recombination through the flanking DNA regions can e.g. be achieved by screening for the absence of sequences present in the transforming DNA but located outside of the flanking DNA regions. Indeed, presence of sequences from the transforming DNA outside the flanking DNA regions would indicate that the transformed plant cells originate from random DNA insertion. To this end, selectable or screenable markers may be included in the transforming DNA molecule outside of the flanking DNA regions, which can then be used to identify those plant cells which do not have the selectable or screenable markers located outside of the transforming DNA and which may have arisen by homologous recombination through the flanking DNA regions. Alternatively, the transforming DNA molecule may contain selectable markers outside the flanking DNA regions that allow selection for the absence of such genes (negative selectable marker genes).

In another embodiment of the invention, the DNA removal method described herein may be combined with a method for DNA insertion at a preselected site in the genome of a cell, based on non-homologous end-joining.

Accordingly, the invention provides a method for inserting a selected DNA molecule at a predetermined location in the genome, preferably the nuclear genome of a plant cell, comprising the following steps:

Inducing a first double stranded DNA break at a preselected site in the genome of the cell, the preselected site preferably being located within a target DNA sequence;

Introducing a foreign (repair) DNA molecule into the plant cell, whereby the DNA molecule comprises the following operably linked DNA fragments:
  i) the selected DNA molecule of interest;
  ii) A selectable or screenable marker gene preceded or followed by a repeat DNA region having at least 80% sequence identity to one of the genomic DNA regions located adjacent to the preselected site whereby the DNA region is located in direct repeat with the genomic copy thereof upon insertion of the foreign DNA molecule in the preselected site by non-homologous end joining;
  iii) At least one recognition site for a rare cleaving DSBI enzyme located in the region of the foreign DNA comprising the repeat DNA region and the selectable marker gene;

Selecting a population of plant cells comprising the selectable or screenable marker;

Selecting a plant cell wherein the selectable or screenable marker has been introduced by non homologous end-joining at the preselected site and regenerating a plant from the plant cell;

Crossing the regenerated plant or a progeny plant thereof comprising the selectable marker gene with a plant comprising a DSBI enzyme encoding chimeric gene, the chimeric gene comprising the following operably linked DNA segments:
  i) a germline specific promoter;
  ii) a DNA region encoding a double stranded DNA break inducing enzyme recognizing the recognition site located in the DNA of interest;
  iii) a transcription termination and polyadenylation region;

Selecting a progeny plant (F1-plant) comprising the selectable or screenable marker gene and the DSBI enzyme encoding chimeric gene;

Crossing the progeny plant with another plant;

Selecting a population of progeny plants (F2-population) which comprises the DSBI enzyme encoding chimeric gene; and Selecting a progeny plant within the F2 population wherein the selectable or screenable marker gene is deleted by homologous recombination between the repeat DNA region and the genomic DNA regions located adjacent to the preselected site.

The above mentioned method can be conveniently used to interrupt any DNA sequence of choice, such as e.g. a polypeptide coding region, a biologically active RNA encoding DNA sequence, a promoter region, a regulatory region, a recognition site for protein or RNA binding etc.

In this embodiment, events wherein the DNA molecule has been inserted by non-homologous end-joining can be conveniently identified by e.g. a PCR reaction using a primer sequence recognizing a genomic sequence located in the vicinity of the preselected site, and which further preferably does not recognize the foreign DNA, and a primer within the foreign DNA molecule. Upon insertion of the foreign DNA by non-homologous end-joining at the preselected a DNA fragment will be amplified. Such DNA fragment would not be amplified when the foreign DNA is randomly integrated.

Although the use of two flanking DNA sequences may be more efficient in a method for exchanging a target DNA sequence in cells of a plant for a DNA sequence of interest (or a foreign DNA), it is possible to use only one flanking DNA sequence. An embodiment of this method is schematically represented in FIG. 4. The "integration" of the repair DNA will occur via homologous recombination at the side of the repair DNA indicated as flanking DNA sequence, and via non-homologous end-joining at the other side of the repair DNA. The repair DNA may be presented as a linear DNA or converted in the cell to a linear DNA. The direct repeats required for the removal of the selectable or screenable marker are generated during the recombination/integration of the repair DNA. Usually, two sets of direct repeats will be generated, whereby the intrachromosomal homologous recombination through one set of direct repeats will result in the desired target DNA modification, whereas intrachromosomal homologous recombination through the other set of direct repeats will result in the restoration of the original target DNA. The desired target DNA modification may be identified e.g. through screening by PCR amplification and sequence identification, or through any other means conventional in the art to distinguish between different nucleotide sequences.

Thus, the invention also provides a method for exchanging a target DNA sequence in cells of a plant for a DNA sequence of interest (or a foreign DNA) comprising the following steps:

Inducing a first double stranded DNA break at a preselected site in the genome of the cell, the preselected site being located within the target DNA sequence or in the vicinity of the target DNA sequence;

Introducing a repair DNA molecule into the plant cell, whereby the repair DNA molecule comprises the following operably linked DNA fragments:
  i. a DNA molecule having the nucleotide sequence of interest flanked at one side by a DNA region having at least 80% sequence homology, preferably 100% sequence homology to a DNA region in the vicinity of the target DNA sequence and of the preselected site in the genome of the plant cell;
  ii. A selectable or screenable marker gene;
  iii. At least one recognition site for a DSBI enzyme located in the vicinity of the selectable or screenable marker gene, preferably two recognition sites for a DSBI enzyme flanking the selectable or screenable marker gene;

Selecting a population of plant cells comprising the selectable or screenable marker;

Selecting a plant cell wherein the selectable or screenable marker has been introduced by homologous recombination through the flanking DNA region and by non-homologous end joining at the other side of the repair DNA and regenerating a plant from the plant cell;

Crossing the regenerated plant or a progeny plant thereof comprising the selectable marker gene with a plant comprising a DSBI enzyme encoding chimeric gene, the chimeric gene comprising the following operably linked DNA segments:
  i. a germline-specific promoter;
  ii. a DNA region encoding a double stranded DNA break inducing enzyme recognizing the recognition site located in the DNA of interest;
  iii. a transcription termination and polyadenylation region;

Selecting a progeny plant (F1-plant) comprising the selectable or screenable marker gene and the DSBI enzyme encoding chimeric gene;

Crossing the progeny plant with another plant whereby the progeny plant is used as a pollen donor in case the germline specific promoter controls expression in the germline cells leading to pollen formation and wherein the progeny plant is used as female in case the germline specific promoter controls expression in the germline cells leading to ovules;

Selecting a population of progeny plants (F2-population) which comprises the DSBI enzyme encoding chimeric gene; and Selecting a progeny plant within the F2 population wherein the selectable or screenable marker gene is deleted by intrachromosomal homologous recombination between the direct repeats generated by integration of the repair DNA, and wherein the target DNA sequence has been replaced by the DNA sequence of interest.

It will also be appreciated that the methods for exchanging a target DNA sequence in cells of a plant for a DNA sequence of interest or for inserting a DNA sequence at a preselected site in a target DNA sequence as described herein can be further modified to avoid the step of introducing the DSBI enzyme encoding chimeric gene by crossing. To this end, the repair DNA can be introduced directly as described elsewhere herein into a plant comprising a DSBI enzyme encoding chimeric gene as described herein. The methods for removal of a selected part of a DNA sequence of interest as described herein can be modified in a similar way.

It will be appreciated that the means and methods of the invention may be used in any plant capable of reproduction through pollen, including corn, tobacco, cereal plants including wheat, oat, barley, rye, rice, turfgrass, sorghum, millet or sugarcane plants. The methods of the invention can also be applied to any plant (Angiospermae or Gymnospermae) including but not limited to cotton, canola, oilseed rape, soybean, vegetables, potatoes, *Lemna* spp., *Nicotiana* spp., *Arabidopsis*, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

It is also an object of the invention to provide plant cells and plants generated according to the methods of the invention. Gametes, seeds, embryos, either zygotic or somatic, progeny or hybrids of plants comprising the DNA insertion events, which are produced by traditional breeding methods are also included within the scope of the present invention. Such plants may contain a heterologous DNA sequence instead of a target sequence, and will only be different from their progenitor plants by the presence of this heterologous DNA or DNA sequence post exchange.

The plants obtained by the methods described herein may be further crossed by traditional breeding techniques with other plants to obtain progeny plants comprising the targeted DNA insertion events obtained according to the present invention.

The following non-limiting Examples describe the removal of a selected subfragment from an introduced DNA molecule using a double strand DNA break inducing enzyme, such as I-SceI, expressed under control of a microspore specific promoter or a microspore/megaspore specific promoter.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:
SEQ ID NO 1: nucleotide sequence of synthetic I-SceI coding region (UIPAC code).
SEQ ID NO 2: nucleotide sequence of synthetic I-SceI coding region.
SEQ ID NO 3: nucleotide sequence of microspore selective NTM 19 gene including promoter region
SEQ ID NO 4: nucleotide sequence of the T-DNA of pTCV63
SEQ ID NO 5: nucleotide sequence of the T-DNA of pTCV64
SEQ ID NO 6: nucleotide sequence of the T-DNA of pTCV72
SEQ ID NO 7: nucleotide sequence of the BnSKP1γ1 promoter region

EXAMPLES

Removal of a Selectable Marker Gene by Intrachromosomal Homologous Recombination (IHR)

A recombination assay to detect removal of a selected DNA fragment has been developed based on the restoration of an egfp-bar fusion gene after removal of a selectable marker gene (hyg) (~2000 bp) by intrachromosomal homologous recombination (IHR) between directly repeated sequences (part of egfp sequences; either about 300 bp or about 600 bp). One of the repeat sequences is flanked by an I-SceI (and Zinc finger Zif268) recognition site giving the possibility to create a DSB between the repeats. In order to allow the IHR during transition from one generation to another, the I-SceI endonuclease was placed under control of a microspore specific promoter (PNTM19).

Using standard recombinant DNA techniques, the following DNA molecules were constructed for use in the following experiments:
1. pTCV63: with short direct repeat sequences (~300 bp) containing the following operably linked DNA constructs:
    p35S3: a CaMV35S promoter fragment
    egf(short): a first part the eGFP coding sequence comprising a 300 bp overlap with the subsequently named GFP sequence
    a recognition site for I-SceI endonuclease
    a recognition site for Zif268 Zn finger containing DNA binding protein
    pCsVMV: a cassava vein mosaic virus promoter fragment
    hyg: coding region for hygromycin resistance
    3'35S: 3' transcription termination and polyadenylation signal
    gfp(short): the 3' part of the eGFP coding sequence, comprising a direct repeat of 300 bp sequences of the previous egf portion of this plasmid, and wherein the coding region is translationally linked to a bar gene coding region
    3'nos: a 3' transcription termination and polyadenylation signal from the nopaline synthase gene.

This plasmid was introduced into *Agrobacterium tumefaciens* and the resulting strain (A4330) was used to generate transgenic tobacco plants (G7NT001).

2. pTCV64: with long direct repeat sequences (~600 bp) containing the following operably linked DNA constructs:
    p35S3: a CaMV35S promoter
    egf(long): a first part the eGFP coding sequence comprising a 600 bp overlap with the subsequently named gfp sequence
    a recognition site for I-SceI endonuclease
    a recognition site for Zif268 Zn finger containing DNA binding protein
    pCsVMV: a cassava vein mosaic virus promoter
    hyg: coding region for hygromycin resistance
    3'35S: 3' transcription termination and polyadenylation signal
    gfp(long): the 3' part of the efgp coding sequence, comprising a direct repeat of 600 bp sequences of the previous egf construct, and wherein the coding region is translationally linked to a bar gene coding region
    3'nos: a 3' transcription termination and polyadenylation signal from the nopaline synthase gene This plasmid was introduced into *Agrobacterium tumefaciens* and the resulting strain (A4364) was used to generate transgenic tobacco plants (G7NT004)

3. pTCV72:
    pnos: a nopaline synthase promoter
    neo: neomycine phosphotransferase II coding region
    3'ocs: a 3' transcription termination and polyadenylation signal from the octopine synthase gene;
    pNTM19: a microspore specific promoter fragment
    I-SceI: coding region for the endonuclease I-SceI
    3'nos: a 3' transcription termination and polyadenylation signal from the CaMV 35S transcript.

This plasmid was introduced into *Agrobacterium tumefaciens* and the resulting strain (A433 1) was used to generate transgenic tobacco plants (G7NT005).

From three independent single copy transformed tobacco lines of each G7NT001 and G7NT004 crosses have been made with two independent single copy transformed lines comprising the chimeric gene encoding I-SceI under control of a microspore specific promoter (G7NT005) using G7NT005 as male plant whereby the progeny lines were indicated as follows:
G7NT001-0001×G7NT005-0001>04TDNT000001
G7NT001-0002×G7NT005-0001>04TDNT000002
G7NT001-0003×G7NT005-0001>04TDNT000003
G7NT001-0001×G7NT005-0002>04TDNT000004
G7NT001-0002×G7NT005-0002>04TDNT000005
G7NT001-0003×G7NT005-0002>04TDNT000006
G7NT004-0001×G7NT005-0001>04TDNT000007
G7NT004-0002×G7NT005-0001> (no progeny)

G7NT004-0003×G7NT005-0001>04TDNT000012
G7NT004-0001×G7NT005-0002>04TDNT000008
G7NT004-0002×G7NT005-0002>04TDNT000010
G7NT004-0003×G7NT005-0002>04TDNT000011

From each crossing 200 seeds have been sown on Km (200 mg/L), 200 seeds on Hyg (50 mg/L) and 200 seeds on Km(200 mg/L)+Hyg(50 mg/L) to check normal transmission of transgenes. There was a quite normal transmission of the different transgenes for most of the crossings (note that for some crossings contamination problems and seed quality problems were encounter (see following table):

| Line | N° of seedlings resistant to the respective selective agent | | | |
|---|---|---|---|---|
| | n° seedlings/ 50 seeds | n° $Km^R$ seedlings/ 200 seeds | n° $Hyg^R$ seedlings/ 200 seeds | n° $km^R$ + $Hyg^R$ seedlings/ 200 seeds |
| G7NT001-0001 × G7NT005-0001 | 32 | 47/150 | 55 | 28/150 |
| G7NT001-0001 × G7NT005-0002 | 32 | 29 | 51 | 15 |
| G7NT001-0002 × G7NT005-0001 | 32 | 89 | 64 | 59 |
| G7NT001-0002 × G7NT005-0002 | 46 | 69 | 94 | 42 |
| G7NT001-0003 × G7NT005-0001 | 47 | 92 | 93 | 53 |
| G7NT001-0003 × G7NT005-0002 | 48 | 88 | 85 | 47 |
| G7NT004-0001 × G7NT005-0001 | 49 | 92 | 65/150 | 44 |
| G7NT004-0002 × G7NT005-0001 | 47 | 73/150 | 89 | 34/150 |
| G7NT004-0002 × G7NT005-0002 | 49 | 58/150 | 98 | 60 |
| G7NT004-0003 × G7NT005-0001 | 39 | 63 | 69 | 50 |
| G7NT004-0003 × G7NT005-0002 | 45 | 60 | 91 | 22 |

From each of these 12 crossings, a few $Km^R$+$Hyg^R$ progeny plants have been transferred to the greenhouse for being used as pollinator of WT SR1 plants. From these 12 crossings each time three $Km^R$+$Hyg^R$ plants have been used as pollinator of WT SR1 plants according to the following scheme:

SR1 × 04TDNT000001-001
            -002
            -003
SR1 × 04TDNT000002-001
            -002
            -003
SR1 × 04TDNT000003-001
            -002
            -003
SR1 × 04TDNT000004-001
            -002
            -003
SR1 × 04TDNT000005-001
            -002
            -003
SR1 × 04TDNT000006-001
            -002
            -003
SR1 × 04TDNT000007-001
            -002
            -003
SR1 × 04TDNT000012-001
            -002
            -003
SR1 × 04TDNT000008-001
            -002
            -003
SR1 × 04TDNT000010-001
            -002
            -003
SR1 × 04TDNT000011-001
            -002
            -003

From each progeny of these crosses (see following tables) 50 seeds have been sown on non-selective substrate to determine the germination frequency, 50 seeds on kanamycin to determine the transmission rate of the NTM19-I-SceI gene and about 4000 seeds on PPT for determining the frequency of IHR during transition from one generation to the other. The number of $PPT^R$ seedlings which are also $Km^R$ determines whether or not there is an effect of DSB induction by NTM19-ISceI endonuclease on the frequency of IHR during transition from one generation to the other.

The results of the progeny analysis of 22 progenies are summarized in tables A, B and C.

There is a very strong effect of NTM19-I-SceI on the frequency of IHR during transition from one generation to another as all PPTR seedlings are also $Km^R$!

It has to be remarked that a large part of the $PPT^R$ and $GFP^F$ seedlings did not develop further into plants and died off due to the toxic effect of GFP.

TABLE A

| Cross | Germination frequency (n° seedlings/ 50 seeds) | N° $Km^R$ seedlings/ 50 seeds | N° $PPT^R$ and $GFP^F$ seedlings/n° of seeds | N° $Km^R$ seedlings/ N° of $PPT^R$ and $GFP^F$ seedlings screened for $Km^R$ |
|---|---|---|---|---|
| SR1 × 04TDNT000001-001 short repeat | 43 | 24 | 77/4348 (1.77%) | 5/5 |
| SR1 × 04TDNT000001-002 short repeat | 49 | 20 | 79/4835 (1.63%) | 23/23 |
| SR1 × 04TDNT000001-003 short repeat | 47 | 22 | 98/4827 (2.03%) | 27/27 |
| SR1 × 04TDNT000002-001 short repeat | 47 | 23 | 33/4762 (0.69%) | 4/4 |
| SR1 × 04TDNT000004-001 short repeat | 49 | 30 | 123/4798 (2.6%) | 36/36 |
| SR1 × 04TDNT000004-002 short repeat | 48 | 23 | 100/4745 (2.1%) | 32/32 |
| SR1 × 04TDNT000004-003 short repeat | 48 | 15 | 118/4665 (2.5%) | 6/6 |
| SR1 × 04TDNT000005-001 short repeat | 49 | 25 | 94/4665 (2.01%) | 16/16 |

TABLE A-continued

| Cross | Germination frequency (n° seedlings/ 50 seeds) | N° $Km^R$ seedlings/ 50 seeds | N° $PPT^R$ and $GFP^F$ seedlings/n° of seeds | N° $Km^R$ seedlings/ N° of $PPT^R$ and $GFP^F$ seedlings screened for $Km^R$ |
|---|---|---|---|---|
| SR1 × 04TDNT000005-002 short repeat | 48 | 20 | 47/4690 (1%) | 7/7 |
| SR1 × 04TDNT000005-003 short repeat | 48 | 22 | 120/4658 (2.6%) | 16/18 (2 S or R?) |
| SR1 × 04TDNT000006-001 short repeat | 47 | 28 | 136/4665 (2.9%) | 24/24 |
| SR1 × 04TDNT000006-003 short repeat | 49 | 20 | 77/4650 (1.66%) | 12/12 |

TABLE B

| Cross | Germination frequency (n° seedlings/ 50 seeds)* | N° $Km^R$ seedlings/ 50 seeds | N° $Hyg^R$ seedlings/ 50 seeds | N° of $Km^R$ + $Hyg^R$/ 100 seeds | N° $PPT^R$ and $GFP^F$ seedlings/N° of seeds** | N° $Km^R$ seedlings/ N° of $PPT^R$ and $GFP^F$ seedlings screened for $Km^R$ |
|---|---|---|---|---|---|---|
| SR1 × 04TDNT000003-001 short repeat | 23 | 14 | 12 | 13 | 44/4973 (0.89%)** | 33/33 |
| SR1 × 04TDNT000003-003 short repeat | 20 | 16 | 11 | 16 | 46/4857 (0.95%)** | 46/46 |
| SR1 × 04TDNT000007-001 long repeat | 19 | 7 | 7 | 7 | 16/4915 (0.33%)** | 16/16 |
| SR1 × 04TDNT000008-001 long repeat | 28 | 17 | 12 | 12 | 33/4890 (0.7%)** | 33/33 |
| SR1 × 04TDNT000008-003 long repeat | 20 | 7 | 8 | 8 | 33/4840 (0.69%)** | 33/33 |
| SR1 × 04TDNT000012-003 long repeat | 16 | 10 | 9 | 9 | 14/4312 (0.32%)** | 14/14 |

*the progenies mentioned in this table were sown at the same moment. Due to a too drastic sterilization with bleach, there was a bad and irregular germination (for most lines <50%).
**This means that the N° of $PPT^R$ and $GFP^F$ seedlings/N° of seeds is an underestimation with at least a factor 2 as the germination frequency is for most lines less than 50%

TABLE C

| Cross | Germination frequency (n° seedlings/ 50 seeds)* | N° $Km^R$ seedlings/ 50 seeds | N° $Hyg^R$ seedlings/ 50 seeds | N° of $Km^R$ + $Hyg^R$/ 100 seeds | N° $PPT^R$ and $GFP^F$ seedlings/n° of seeds ** | N° $Km^R$ seedlings/ N° of $PPT^R$ and $GFP^F$ seedlings screened for $Km^{R*}$ |
|---|---|---|---|---|---|---|
| SR1 × 04TDNT000002-002 short repeat | 50 | 20 | 26 | 9 | 7/1330 (0.5%) | NT* |
| SR1 × 04TDNT000002-003 short repeat | 50 | 30 | 18 | 25 | 9/1355 (0.66%) | NT* |
| SR1 × 04TDNT000003-002 short repeat | 50 | 20 | 21 | 25 | 24/1389 (1.7%) | NT* |
| SR1 × 04TDNT000007-003 long repeat | 50 | 25 | 25 | 17 | 3/1346 (0.2%) | NT* |

*NT: not tested yet

Moreover all $PPT^R$ and $GFP^F$ seedlings are indeed hygromycin sensitive, demonstrating the hyg gene has indeed been removed by intrachromosomal recombination in the IHR locus.

| Cross | N° of $Hyg^R$ seedlings/N° of $PPT^R$ and $GFP^F$ seedlings screened for $Hyg^R$ |
|---|---|
| SR1 × 04TDNT000012-003 | 0/11 |
| SR1 × 04TDNT000008-001 | 0/12 |
| SR1 × 04TDNT000008-003 | 0/11 |
| SR1 × 04TDNT000001-002 | 0/8 |
| SR1 × 04TDNT000005-003 | 0/7 |
| SR1 × 04TDNT000006-003 | 0/7 |

From the segregation analysis of 18 progeny populations, it can be concluded that there is a very strong effect of NTM19-I-SceI on the frequency of IHR during transition from one generation to another as all $PPT^R$ seedlings are also $Km^R$.

The progeny of a crossing between SR1 (female) and 04TDNT00000X-00Y will normally segregate into:
- 25% with only NTMI9-ISceI endonuclease
- 25% with only the IHR construct
- 25% with both NTM19-1-SceI endonuclease+IHR construct
- 25% neither NTM19-I-SceI endonuclease nor IHR construct The fact that all $PPT^R$ seedlings are also $Km^R$ shows that all IHR recombinants occur only in the fraction which contains both the I-SceI endonuclease under control of a NTM19 microspore specific promoter as well as the IHR construct. Our results show that in the best case up to 11% of the microspores which contain both NTM19-ISceI endonuclease+IHR construct has undergone intrachromosomal homologous recombination resulting in the restoration of a defective egfp-bar fusion gene (SR1×04TDNT000006-001). As no IHR recombinants resulting in a functional egfp-bar gene were obtained in the fraction which contains only the IHR construct, we may conclude that either spontaneous IHR (in absence of targeted DSB induction in the microspores) does not occur or if spontaneous IHR does occur, it does not result in the restoration of a defective egfp-bar fusion gene. In contrast, DSB-induced IHR in the microspores allows more precise intrachromosomal homologous recombination resulting in the restoration of a defective egfp-bar fusion gene.

Sequence analysis showed that no footprints are left after removal of the selectable marker mediated by DSB-induced IHR in the microspores.

Removal of a Selectable Marker Gene by Intrachromosomal Homologous Recombination (IHR) in *Brassica* spp.

*Agrobacterium tumefaciens* strains comprising respectively the vectors PTCV64 and pTCV63 are used to generate transgenic *Brassica napus* plants.

A new T-DNA vector is developed based on pTCV72, wherein the pNTM19 microspore specific promoter fragment is replaced by the promoter having the sequence of SEQ ID NO 7.

pnos: a nopaline synthase promoter
neo: neomycine phosphotransferase II coding region
3'ocs: a 3' transcription termination and polyadenylation signal from the octopine synthase gene;
pSKIP1γ1: a germline specific promoter fragment
I-SceI: coding region for the endonuclease I-SceI
3'nos: a 3' transcription termination and polyadenylation signal from the CaMV 35S transcript This T-DNA vector is introduced into *Agrobacterium tumefaciens* and the resulting strain is used to generate transgenic *Brassica napus* plants.

The transgenic *Brassica napus* plants comprising the T-DNAs of respectively pTCV63 and pTCV64 are crossed with the *Brassica napus* plants comprising the T-DNA vector with the chimeric I-SceI encoding gene under control of the SKIP1γ1 promoter and KmR, HygR progeny plants are selected. These plants are either crossed with non-transgenic *B. napus* plants (wherein the transgenic plants can be used both as male or female partners) or selfed and progeny plants are selected for resistance to phosphinotricin and analyzed for restoration of the GFP coding region.

*Agrobacterium* strains comprising T-DNA vectors pTCV63 or pTCV64 are also used to transform transgenic *Brassica napus* plants comprising the T-DNA vector with the chimeric I-SceI encoding gene under control of the SKIP1γ1 promoter and KmR, HygR transgenic plants are selected and further used as described in the preceding paragraph.

The invention claimed is:
1. A method for exchanging a target DNA sequence in the genome of a plant for a DNA sequence of interest comprising
   a. inducing a double stranded DNA break at a preselected site in the genome of a cell of a plant, said preselected site being located within said target DNA sequence or in the vicinity of said target DNA sequence;
   b. introducing a repair DNA molecule of interest into said plant cell, said DNA molecule comprising
      i. said DNA sequence of interest located between two flanking DNA regions being at least 10 nucleotides in length and having at least 80% sequence homology to a DNA region flanking said target DNA sequence;
      ii. a selectable or screenable marker gene located between said flanking DNA regions, said selectable or screenable marker gene further being located between one of said flanking DNA regions and a copy of at least part of said one of said flanking DNA regions in direct repeat orientation;
      iii. at least one recognition site for a DSBI enzyme located between said one of said flanking DNA regions and said copy of at least part of said flanking DNA region;
   c. selecting a population of plant cells comprising said selectable or screenable marker;
   d. selecting a plant cell wherein said selectable or screenable marker has been introduced by homologous recombination through said flanking DNA regions and regenerating a plant from said plant cell;
   e. crossing said regenerated plant or a progeny plant thereof comprising said selectable marker gene with a plant comprising a chimeric gene encoding a DSBI enzyme recognizing said recognition site located in said repair DNA molecule of interest to obtain a population of F1 progeny plants, said chimeric gene comprising the following operably linked DNA segments:
      i. a germline specific promoter, provided that said promoter does not comprise the nucleotide sequence of SEQ ID No 3 from position 1-992;
      ii. a DNA region encoding said DSBI enzyme recognizing said recognition site located in said repair DNA molecule of interest;
      iii. a transcription termination and polyadenylation region;
   f. selecting an F1 progeny plant comprising said selectable or screenable marker gene and said DSBI enzyme encoding chimeric gene;
   g. crossing said progeny plant with a wild type plant to obtain a population of F2 progeny plants;
   h. selecting a population of F2 progeny plants which comprises said DSBI enzyme encoding chimeric gene; and
   i. selecting an F2 progeny plant wherein said selectable or screenable marker gene is deleted by homologous recombination between said one of the flanking DNA regions and a partial flanking DNA region comprising part of said one of the flanking DNA regions.
2. The method of claim 1, wherein said double stranded break at said preselected site is induced by introduction of a first DSBI enzyme, said first DSBI enzyme not recognizing said recognition site for a DSBI enzyme located in said repair DNA molecule of interest.
3. The method of claim 2, wherein said first DSBI enzyme and said DSBI enzyme recognizing said recognition site located in said repair DNA molecule of interest are two different DSBI enzymes, wherein said DSBI enzymes are I-Sce, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I or a chimeric endonuclease comprising a Zn finger DNA binding domain and a DNA cleavage domain.
4. The method of claim 1, wherein said DSBI enzyme recognizing said recognition site located in said repair DNA molecule of interest is I-SceI.
5. The method of claim 4, wherein said DNA region encoding said DSBI enzyme comprises the nucleotide sequence of SEQ ID No 1 or SEQ ID No 2.
6. The method of claim 1, wherein said germline-specific promoter comprises the nucleotide sequence of SEQ ID No 7.
7. The method of claim 1, wherein said germline-specific promoter comprises an *Arabidopsis* egg apparatus (EA) specific enhancer, fused to a minimal promoter element; *Arabidopsis* TAG1 promoter; *Arabidopsis* Duo1 promoter; a promoter from LGC1 from Lilium; a promoter from the ERCC1 homolog expressed in male sperm cells; a histone gcH3 promoter of *Lilium longiflorum*; Zmea1 promoter; a ZmES promoter; a BnM1 promoter; or a BnM3.4 promoter.
8. The method of claim 1, wherein said DSBI enzyme encoding chimeric gene comprises the nucleotide sequence of SEQ ID No. 6 from nucleotide 1941 to 3913.
9. The method of claim 1, further comprising the steps of
   j. crossing the F2 progeny plant wherein the subsequence of the DNA molecule has been deleted, with a wild type plant;
   k. obtaining a population of F3 progeny plants; and
   l. selecting from said F3 population plants which do not contain said DSBI enzyme encoding chimeric gene.
10. A method for exchanging a target DNA sequence in the genome of a plant for a DNA sequence of interest comprising
   a) inducing a double stranded DNA break at a preselected site in the genome of the cell, the preselected site being located within the target DNA sequence or in the vicinity of said target DNA sequence;
   b) introducing a repair DNA molecule of interest into the plant cell, whereby the repair DNA molecule comprises the following operably linked DNA fragments:
      i) a DNA molecule comprising the nucleotide sequence of interest flanked at one side by a DNA region being at least 10 nt in length and having at least 80% sequence homology to a DNA region flanking said target DNA sequence having at least 80% sequence homology to a DNA region in the vicinity of the target DNA sequence and of the preselected site in the genome of the plant cell;
      ii) a selectable or screenable marker gene;
      iii) at least one recognition site for a DSBI enzyme located in the vicinity of the selectable or screenable marker gene;
   c) selecting a population of plant cells comprising the selectable or screenable marker;
   d) selecting a plant cell wherein the selectable or screenable marker has been introduced by homologous recombination through the flanking DNA region and by non-homologous end joining at the other side of the repair DNA and regenerating a plant from the plant cell;
   e) crossing the regenerated plant or a progeny plant thereof comprising the selectable marker gene with a plant comprising a chimeric gene encoding a DSBI enzyme recognizing said recognition site located in said repair DNA molecule of interest to obtain a population of F1 plants, the chimeric gene comprising the following operably linked DNA segments:
  i) a germline-specific promoter;
  ii) a DNA region encoding said DSBI enzyme recognizing said recognition site located in said repair DNA molecule of interest;
  iii) a transcription termination and polyadenylation region;
f) selecting an F1 progeny plant comprising the selectable or screenable marker gene and the DSBI enzyme encoding chimeric gene;
g) crossing the progeny plant with a wild type plant to obtain a population of F2 plants, wherein the progeny plant is used as a pollen donor in case the germline specific promoter controls expression in the germline cells leading to pollen formation and wherein the progeny plant is used as female in case the germline specific promoter controls expression in the germline cells leading to ovules;
h) selecting a population of F2 progeny plants which comprises the DSBI enzyme encoding chimeric gene; and
i) selecting a progeny plant within said selected F2 population wherein the selectable or screenable marker gene is deleted by intrachromosomal homologous recombination between the direct repeats generated by integration of the repair DNA molecule of interest, and wherein the target DNA sequence has been replaced by said DNA sequence of interest.

11. The method of claim 10, wherein said double stranded break at said preselected site is induced by introduction of a first DSBI enzyme, said first DSBI enzyme not recognizing said recognition site for a DSBI enzyme located in said repair DNA molecule of interest.

12. The method of claim 11, wherein said first DSBI enzyme and said DSBI enzyme recognizing said recognition site located in said repair DNA molecule of interest are two different DSBI enzymes, and said two different DSBI enzymes are I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, or a chimeric endonuclease comprising a Zn finger DNA binding domain and a DNA cleavage domain.

13. The method of claim 10, wherein said DSBI enzyme recognizing said recognition site located in said repair DNA molecule of interest is I-SceI.

14. The method of claim 13, wherein said DNA region encoding said DSBI enzyme comprises the nucleotide sequence of SEQ ID No 1 or SEQ ID No 2.

15. The method of claim 10, wherein said germline-specific promoter comprises the nucleotide sequence of SEQ ID No 7 or SEQ ID No 3.

16. The method of claim 10, wherein said germline-specific promoter comprises an *Arabidopsis* egg apparatus (EA) specific enhancer, fused to a minimal promoter element; *Arabidopsis* TAG1 promoter; *Arabidopsis* Duo1 promoter; a promoter from LGC1 from Lilium; a promoter from the ERCC1 homolog expressed in male sperm cells; a histone gcH3 promoter of *Lilium longiflorum*; Zmea1 promoter; a ZmES promoter; a BnM1 promoter; or a BnM3.4 promoter.

17. The method of claim 10, wherein said DSBI encoding chimeric gene comprises the nucleotide sequence of SEQ ID No. 6 from nucleotide position 1941 to nucleotide position 3913.

18. The method of claim 10, further comprising the steps of
  i) crossing the F2 progeny plant wherein the subsequence of the DNA molecule has been deleted, with a wild type plant; and
  ii) obtaining a population of F3 progeny plants and;
  iii) selecting plants which do not contain said DSBI enzyme encoding chimeric gene.

19. A method for exchanging a target DNA sequence in the genome of a plant for a DNA sequence of interest comprising
  a. providing a plant comprising a DSBI enzyme encoding chimeric gene, said chimeric gene comprising the following operably linked DNA segments:
    i. a germline specific promoter, provided that said promoter does not comprise the nucleotide sequence of SEQ ID No 3 from position 1-992;
    ii. a DNA region encoding a double stranded DNA break inducing enzyme recognizing a recognition site located in said DNA of interest;
    iii. a transcription termination and polyadenylation region;
  b. inducing a double stranded DNA break at a preselected site in the genome of a cell of a plant, said preselected site being located within said target DNA sequence or in the vicinity of said target DNA sequence;
  c. introducing a repair DNA molecule of interest into said plant cell, said DNA molecule comprising
    said DNA sequence of interest located between two flanking DNA regions being at least 10 nt in length and having at least 80% sequence homology to a DNA region flanking said target DNA sequence having at least 80% sequence homology to a DNA region flanking said target DNA sequence;
    ii. a selectable or screenable marker gene located between said flanking DNA regions, said selectable or screenable marker gene further being located between one of the flanking DNA regions and a copy of at least part of said one of the flanking DNA regions in direct repeat orientation;
    iii. at least one recognition site for said DSBI enzyme encoded by said chimeric gene, said recognition site being located between said one of the flanking DNA regions and said copy of at least part of said partial flanking DNA region;
  d. selecting a population of plant cells comprising said selectable or screenable marker;
  e. selecting a plant cell wherein said selectable or screenable marker has been introduced by homologous recombination through said flanking DNA regions and regenerating a plant from said plant cell;
  f. crossing or selfing said plant to obtain a population of progeny plants;
  g. selecting a progeny plant wherein said selectable or screenable marker gene is deleted by homologous recombination between said one of the flanking DNA regions and said partial flanking DNA region comprising part of said one of the flanking DNA regions.

20. A method for exchanging a target DNA sequence in the genome of a plant for a DNA sequence of interest comprising
  a) providing a plant comprising a DSBI enzyme encoding chimeric gene, the chimeric gene comprising the following operably linked DNA segments:

i) a germline-specific promoter;
ii) a DNA region encoding a DSBI enzyme recognizing a recognition site located in the DNA of interest;
iii) a transcription termination and polyadenylation region;
b) inducing a double stranded DNA break at a preselected site in the genome of the cell, the preselected site being located within the target DNA sequence or in the vicinity of said target DNA sequence;
c) introducing a repair DNA molecule of interest into the plant cell, wherein the repair DNA molecule of interest comprises the following operably linked DNA fragments:
  i) a DNA molecule comprising the nucleotide sequence of interest flanked at one side by a DNA region of at least 10 nucleotides having at least 80% sequence homology to a DNA region in the vicinity of the target DNA sequence and of the preselected site in the genome of the plant cell;
  ii) a selectable or screenable marker gene;
  iii) at least one recognition site for said DSBI enzyme encoded by said chimeric gene, said recognition site being located in the vicinity of the selectable or screenable marker gene;
d) selecting a population of plant cells comprising the selectable or screenable marker;
e) selecting a plant cell wherein the selectable or screenable marker has been introduced by homologous recombination through the flanking DNA region and by non-homologous end joining at the other side of the repair DNA and regenerating a plant from the plant cell;
f) crossing or selfing the regenerated plant or a progeny plant thereof comprising the selectable marker gene to obtain a population of progeny plants;
g) selecting a progeny plant within said population wherein the selectable or screenable marker gene is deleted by intrachromosomal homologous recombination between the direct repeats generated by integration of the repair DNA, and wherein the target DNA sequence has been replaced by said DNA sequence of interest.

21. The method of claim 1, wherein said DNA sequence of interest flanks said preselected site in the genome of said plant cell.

22. The method of claim 10, wherein at least two recognition sites for a DSBI enzyme are located in the vicinity of the selectable or screenable marker gene.

23. The method of claim 10, wherein said flanking DNA region has 100% sequence homology to said DNA region in the vicinity of the target DNA sequence and of the preselected site.

24. The method of claim 20, wherein at least two recognition sites for a DSBI enzyme are located in the vicinity of the selectable or screenable marker gene.

25. The method of claim 20, wherein said flanking DNA region has 100% sequence homology to said DNA region in the vicinity of the target DNA sequence and of the preselected site.

26. The method of claim 1, wherein said flanking DNA regions are at least 50 nucleotides in length.

27. The method of claim 10, wherein said flanking DNA region is at least 50 nucleotides in length.

28. The method of claim 19, wherein said flanking DNA regions are at least 50 nucleotides in length.

29. The method of claim 20, wherein said flanking DNA region is at least 50 nucleotides in length.

* * * * *

SEQUENCE LISTING

```
<160> NUMBER OF SEQ ID NOS: 7

<210> SEQ ID NO 1
<211> LENGTH: 732
<212> TYPE: DNA
<213> ORGANISM: Artificial Sequence
<220> FEATURE:
<223> OTHER INFORMATION: synthetic I-SceI coding region (UIPAC)
<220> FEATURE:
<221> NAME/KEY: variation
<222> LOCATION: (25)..(27)
<223> OTHER INFORMATION: AGA
<220> FEATURE:
<221> NAME/KEY: variation
<222> LOCATION: (73)..(75)
<223> OTHER INFORMATION: AGC
<220> FEATURE:
<221> NAME/KEY: variation
<222> LOCATION: (97)..(99)
<223> OTHER INFORMATION: AGC
<220> FEATURE:
<221> NAME/KEY: variation
<222> LOCATION: (169)..(171)
<223> OTHER INFORMATION: AGA
<220> FEATURE:
<221> NAME/KEY: variation
<222> LOCATION: (172)..(174)
<223> OTHER INFORMATION: AGC
<220> FEATURE:
<221> NAME/KEY: variation
<222> LOCATION: (175)..(177)
<223> OTHER INFORMATION: AGA
<220> FEATURE:
<221> NAME/KEY: variation
<222> LOCATION: (268)..(270)
<223> OTHER INFORMATION: AGC
<220> FEATURE:
<221> NAME/KEY: variation
<222> LOCATION: (289)..(291)
<223> OTHER INFORMATION: AGA
<220> FEATURE:
<221> NAME/KEY: variation
<222> LOCATION: (436)..(438)
<223> OTHER INFORMATION: AGC
```

```
<220> FEATURE:
<221> NAME/KEY: variation
<222> LOCATION: (490)..(492)
<223> OTHER INFORMATION: AGC
<220> FEATURE:
<221> NAME/KEY: variation
<222> LOCATION: (502)..(504)
<223> OTHER INFORMATION: AGC
<220> FEATURE:
<221> NAME/KEY: variation
<222> LOCATION: (523)..(525)
<223> OTHER INFORMATION: AGC
<220> FEATURE:
<221> NAME/KEY: variation
<222> LOCATION: (565)..(567)
<223> OTHER INFORMATION: AGA
<220> FEATURE:
<221> NAME/KEY: variation
<222> LOCATION: (631)..(633)
<223> OTHER INFORMATION: AGC
<220> FEATURE:
<221> NAME/KEY: variation
<222> LOCATION: (637)..(639)
<223> OTHER INFORMATION: AGC
<220> FEATURE:
<221> NAME/KEY: variation
<222> LOCATION: (712)..(714)
<223> OTHER INFORMATION: AGC
<220> FEATURE:
<221> NAME/KEY: variation
<222> LOCATION: (715)..(717)
<223> OTHER INFORMATION: AGC

<400> SEQUENCE: 1
atggcyaarc chcchaaraa raarcgsaaa gtsaacatya araaraacca ggtsatgaac      60
ctsggmccha actcmaarct sctsaargag tacaartcmc arctsatyga rctsaacaty    120
garcarttcg argcyggmat cggmctsaty ctsggmgayg cytacatycg stcmcgsgay    180
garggmaara cytactgyat gcagttcgar tggaaraaca argcytacat ggaycaygts    240
tgyctsctst acgaycartg ggtsctstcm cchcchcaya araargarcg sgtsaaccay    300
ctsggmaacc tsgtsatyac ytggggmgcy caracyttca arcaycargc yttcaacaar    360
ctsgcsaacc tsttcatyct saacaacaar aaracyatyc chaacaacct sgtsgaraac    420
tacctsacyc cyatgtcmct sgcytactgg ttcatggayg ayggmggmaa rtgggaytac    480
aacaaraact cmacyaacaa rtcmatygts ctsaacacyc artcmttcac yttcgargar    540
gtsgartacc tsgtsaargg mctscgsaac aarttccarc tsaactgyta cgtsaagaty    600
aacaaraaca arccyatyat ctacatygay tcmatgtcmt acctsatytt ctacaaccts    660
atyaarccht acctsatycc hcaratgatg tacaarctsc chaacacyat ytcmtcmgar    720
acyttcctsa ar                                                        732

<210> SEQ ID NO 2
<211> LENGTH: 732
<212> TYPE: DNA
<213> ORGANISM: Artificial Sequence
<220> FEATURE:
<223> OTHER INFORMATION: synthetic I-SceI coding region

<400> SEQUENCE: 2
atggccaagc tcccaagaa gaagcgcaaa gtgaacatca agaagaacca ggtgatgaac       60
ctgggaccta acagcaagct cctgaaggag tacaagagcc agctgatcga actgaacatc    120
gagcagttcg aagctggcat cggcctgatc ctgggcgatg cctacatcag atcccgggac    180
gaaggcaaga cctactgcat gcagttcgag tggaagaaca aggcctacat ggaccacgtg    240
tgtctgctgt acgaccagtg ggtcctgagc cctcctcaca agaaggagcg cgtgaaccat    300
```

```
ctgggcaacc tcgtgatcac ctggggagcc cagaccttca agcaccaggc cttcaacaag      360
ctggccaacc tgttcatcgt gaacaacaag aagaccatcc ccaacaacct cgtggagaac      420
tacctcactc ccatgagcct ggcctactgg ttcatggacg acggaggcaa gtgggactac      480
aacaagaaca gcaccaacaa gtcaattgtg ctgaacaccc aaagcttcac cttcgaagaa      540
gtggagtacc tcgtcaaggg cctgcgcaac aagttccagc tgaactgcta cgtgaagatc      600
aacaagaaca agcctatcat ctacatcgac agcatgagct acctgatctt ctacaacctg      660
atcaagccat acctgatccc tcagatgatg tacaagctgc ccaacaccat cagcagcgag      720
accttcctga ag                                                          732

<210> SEQ ID NO 3
<211> LENGTH: 1618
<212> TYPE: DNA
<213> ORGANISM: Nicotiana tabacum
<220> FEATURE:
<221> NAME/KEY: TATA_signal
<222> LOCATION: (919)..(922)
<220> FEATURE:
<221> NAME/KEY: mRNA
<222> LOCATION: (954)..(1573)
<220> FEATURE:
<221> NAME/KEY: gene
<222> LOCATION: (993)..(1271)
<223> OTHER INFORMATION: NTM19
<220> FEATURE:
<221> NAME/KEY: misc_feature
<222> LOCATION: (993)..(1271)
<223> OTHER INFORMATION: coding region

<400> SEQUENCE: 3
gatccagatt tatagggtcc taatgcgggt actgaacacc aggtgggaaa caaaaaatat       60
acagaacaac tcctttagaa tttacaattt ttgagcgtgt tggcttggta cgattctact      120
tttcatatct ctcgtcatct cctaactcct atggttcacc agccaccgat taattatgac      180
accgctaaca aaaatcttgc gacgacattg agagaaattt cttttcataa attggtaatt      240
cgtacatcat ttataggcgt tagctataac cttttagtta gtgaatacaa tacttttgc      300 tattattatg taacttttag atatgaattt actttcaaaa aaaaaaaag gatcgatgtt      360 ggttatcaac taaggaccaa ccactttgga cgtctcacca ctaagttaaa taatcacctt      420
tgttctcgaa aaaaccccca aaagtgttaa aatgcttttc atatcataat caaacaacgt      480
gattaataaa atctattaag ttaatagaag tagggaataa atcgggcaaa agaatttgat      540
acaaaccaaa ccggtcaaaa aagctagtat tcatataaat ggactataca agttaatacc      600
agctagcaga aattaaatag tttattaagt tgattacaaa acaattcctc atttaaaaaa      660
agttaatgta atcaagagat cttttgcttc taattgatca gacgaggacc cctcttattt      720 atttctttt tcatataaga ttttgaatag atataggaa atcttgttca ctctttatct      780
acttcaaatt gcatgcattt taagaattct ctttgtatgc aaacttcagt atttatgatt      840
gacataaatc aatattcata tcttcgataa agttaataac tctcctaata cttatgaata      900
tctcttcctt tacaacccta taaaaccccc cactatagct accttcataa ttcatcttag      960
agtaccaacc ctaaatttct tagtgattaa ccatggctaa gaaaagtctc acttttctca     1020
tttgcatttt cctacttctc aatttatgtt ttgcaattga gaacgtagaa actatgcaaa     1080
aatcggattc atcgtcacaa gataaagaat tagattggtt tcatccgtgg ttccatccac     1140
atccatggtg gctacatcca catccatggc cattcgttca tccgccaatg ccagctggcg     1200
gttttcatca tgcatggcca ttccccccatc caccgatgcc tgctggtggt tttaagtttc     1260
```

```
ctcatcaata atttcatcgt catccatggc cattcatgca tccaccagtt ccatctccac    1320
ctaaaggaga caagaattaa ttgaaaatat gaagagaagt gttggatcaa catcttattg    1380
atcacatatt tttctttagg ttaatatctt taggatttat gtcttaggtt attttgata     1440 aaaattaaaa taaatgatcg ttctagggta gttattataa tttcttagat ttttccaagt    1500
agctttcgat ggtagaaatg ttattaattt gattcggctt atcatgaaat aaaatccgta    1560
gtattattgc tttagctttt atgatttgta gttattttat gttgattgtt ctccattt     1618
```

```
<210> SEQ ID NO 4
<211> LENGTH: 4683
<212> TYPE: DNA
<213> ORGANISM: Artificial Sequence
<220> FEATURE:
<223> OTHER INFORMATION: T-DNA of pTCV63
<220> FEATURE:
<221> NAME/KEY: misc_feature
<222> LOCATION: (191)..(222)
<223> OTHER INFORMATION: Right T-DNA border
<220> FEATURE:
<221> NAME/KEY: promoter
<222> LOCATION: (270)..(818)
<223> OTHER INFORMATION: CaMV35S promoter region
<220> FEATURE:
<221> NAME/KEY: misc_feature
<222> LOCATION: (819)..(875)
<223> OTHER INFORMATION: Cab22Leader sequence
<220> FEATURE:
<221> NAME/KEY: misc_feature
<222> LOCATION: (885)..(1391)
<223> OTHER INFORMATION: 5' part of the eGFP coding region
<220> FEATURE:
<221> NAME/KEY: misc_feature
<222> LOCATION: (1392)..(1409)
<223> OTHER INFORMATION: I-SceI recognition site
<220> FEATURE:
<221> NAME/KEY: misc_feature
<222> LOCATION: (1411)..(1419)
<223> OTHER INFORMATION: Zif268 recognition site
<220> FEATURE:
<221> NAME/KEY: misc_feature
<222> LOCATION: (1433)..(1671)
<223> OTHER INFORMATION: 3' 35S polyadenylation region (complement)
<220> FEATURE:
<221> NAME/KEY: misc_feature
<222> LOCATION: (1683)..(2708)
<223> OTHER INFORMATION: hygromycin resistance coding region
      (complement)
<220> FEATURE:
<221> NAME/KEY: misc_feature
<222> LOCATION: (2715)..(2787)
<223> OTHER INFORMATION: CsVMV leader region (complement)
<220> FEATURE:
<221> NAME/KEY: promoter
<222> LOCATION: (2788)..(3227)
<223> OTHER INFORMATION: CsVMV promoter fragment (complement)
<220> FEATURE:
<221> NAME/KEY: misc_feature
<222> LOCATION: (3269)..(3787)
<223> OTHER INFORMATION: 3' part of eGFP
<220> FEATURE:
<221> NAME/KEY: misc_feature
<222> LOCATION: (3788)..(4339)
<223> OTHER INFORMATION: phosphinotricin acetyltransferase coding region
<220> FEATURE:
<221> NAME/KEY: terminator
<222> LOCATION: (4341)..(4549)
<223> OTHER INFORMATION: 3' nos: transcription termination and
      polyadenylation region
<220> FEATURE:
<221> NAME/KEY: misc_feature
<222> LOCATION: (4659)..(4683)
<223> OTHER INFORMATION: right T-DNA border

<400> SEQUENCE: 4
```

```
agattcgaag ctcggtcccg tgggtgttct gtcgtctcgt tgtacaacga aatccattcc      60
cattccgcgc tcaagatggc ttcccctcgg cagttcatca gggctaaatc aatctagccg     120
acttgtccgg tgaaatgggc tgcactccaa cagaaacaat caaacaaaca tacacagcga     180
cttattcaca cgcgacaaat tacaacggta tatatcctgc cagtactcgg ccgtcgacct     240
gcaggcaatt ggtacctacg tatgcatggc gcgccatatg caccatacat ggagtcaaaa     300
attcagatcg aggatctaac agaactcgcc gtgaagactg gcgaacagtt catacagagt     360
cttttacgac tcaatgacaa gaagaaaatc ttcgtcaaca tggtggagca cgacactctc     420
gtctactcca agaatatcaa agatacagtc tcagaagacc aaagggctat tgagactttt     480
caacaaaggg taatatcggg aaacctcctc ggattccatt gcccagctat ctgtcacttc     540
atcaaaagga cagtagaaaa ggaaggtggc acctacaaat gccatcattg cgataaagga     600
aaggctatcg ttcaagatgc ctctgccgac agtggtccca agatggaccc ccacccacg      660
aggagcatcg tggaaaaaga agacgttcca accacgtctt caaagcaagt ggattgatgt     720
gatatctcca ctgacgtaag ggatgacgca caatcccact atccttcgca agacccttcc     780
tctatataag gaagttcatt tcatttggag aggactcgag ctcatttctc tattacttca     840
gccataacaa aagaactctt ttctcttctt attaaaccaa aaccatggtg agcaagggcg     900
aggagctgtt caccggggtg gtgcccatcc tggtcgagct ggacggcgac gtaaacggcc     960
acaagttcag cgtgtccggc gagggcgagg gcgatgccac ctacggcaag ctgaccctga    1020
agttcatctg caccaccggc aagctgcccg tgccctggcc caccctcgtg accaccctga    1080
cctacggcgt gcagtgcttc agccgctacc ccgaccacat gaagcagcac gacttcttca    1140
agtccgccat gcccgaaggc tacgtccagg agcgcaccat cttcttcaag gacgacggca    1200
actacaagac ccgcgccgag gtgaagttcg agggcgacac cctggtgaac cgcatcgagc    1260
tgaagggcat cgacttcaag gaggacggca acatcctggg gcacaagctg gagtacaact    1320
acaacagcca caacgtctat atcatggccg acaagcagaa gaacggcatc aaggtgaact    1380
tcaagatccg ctagggataa cagggtaatg cgtgggcga ccgtcccgg ccgctgtacc     1440
atgcatgatc tggatttag tactggattt tggttttagg aattagaaat tttattgata    1500
gaagtatttt acaaatacaa atacatacta agggtttctt atatgctcaa cacatgagcg    1560
aaaccctata ggaaccctaa ttcccttatc tgggaactac tcacacatta ttatgagaa    1620
aatagagaga gatagatttg tagagagaga ctggtgattt cagcgtgtcc aagcttgata    1680
tcctattcct ttgccctcgg acgagtgctg gggcgtcggt ttccactatc ggcgagtact    1740
tctacacagc catcggtcca gacggccgcg cttctgcggg cgatttgtgt acgcccgaca    1800
gtcccggctc cggatcggac gattgcgtcg catcgaccct gcgcccaagc tgcatcatcg    1860
aaattgccgt caaccaagct ctgatagagt tggtcaagac caatgcggag catatacgcc    1920
cggagccgcg cgatcctgc aagctccgga tgcctccgct cgaagtagcg cgtctgctgc    1980
tccatacaag ccaaccacgg cctcagaag aagatgttgg cgacctcgta ttgggaatcc    2040
ccgaacatcg cctcgctcca gtcaatgacc gctgttatgc ggccattgtc cgtcaggaca    2100
ttgttggagc cgaaatccgc gtgcacgagg tgccggactt cggggcagtc ctcggcccaa    2160
agcatcagct catcgagagc ctgcgcgacg acgcactga cggtgtcgtc catcacagtt    2220
tgccagtgat acacatgggg atcagcaatc gcgcatatga aatcacgcca tgtagtgtat    2280
tgaccgattc cttgcggtcc gaatgggccg aaccgctcg tctggctaag atcggccgca    2340
gcgatcgcat ccatggcctc cgcgaccggc tgcagaacag cgggcagttc ggtttcaggc    2400
```

```
aggtcttgca acgtgacacc ctgtgcacgg cgggagatgc aataggtcag gctctcgctg   2460
aattccccaa tgtcaagcac ttccggaatc gggagcgcgg ccgatgcaaa gtgccgataa   2520
acataacgat ctttgtagaa accatcggcg cagctattta cccgcaggac atatccacgc   2580
cctcctacat cgaagctgaa agcacgagat tcttcgccct ccgagagctg catcaggtcg   2640
gagacgctgt cgaactttc gatcagaaac ttctcgacag acgtcgcggt gagttcaggc   2700
tttttcatct cgagacaaac ttacaaattt ctctgaagtt gtatcctcag tacttcaaag   2760
aaaatagctt acaccaaatt ttttcttgtt ttcacaaatg ccgaacttgg ttccttatat   2820
aggaaaactc aagggcaaaa atgacacgga aaaatataaa aggataagta gtgggggata   2880
agattccttt gtgataaggt tactttccgc ccttacattt tccaccttac atgtgtcctc   2940
tatgtctctt tcacaatcac cgaccttatc ttcttctttt cattgttgtc gtcagtgctt   3000
acgtcttcaa gattcttttc ttcgcctggt tcttcttttt caatttctac gtattcttct   3060
tcgtattctg gcagtatagg atcttgtatc tgtacattct tcattttga acataggttg    3120
catatgtgcc gcatattgat ctgcttcttg ctgagctcac ataatacttc catagttttt   3180
cccgtaaaca ttggattctt gatgctacat cttggataat taccttcggc gcgccatgca   3240
tacgtaggta ccaattgccg ggaccggtta cggcgtgcag tgcttcagcc gctaccccga   3300
ccacatgaag cagcacgact tcttcaagtc cgccatgccc gaaggctacg tccaggagcg   3360
caccatcttc ttcaaggacg acggcaacta caagacccgc gccgaggtga agttcgaggg   3420
cgacaccctg gtgaaccgca tcgagctgaa gggcatcgac ttcaaggagg acggcaacat   3480
cctggggcac aagctggagt acaactacaa cagccacaac gtctatatca tggccgacaa   3540
gcagaagaac ggcatcaagg tgaacttcaa gatccgccac aacatcgagg acggcagcgt   3600
gcagctcgcc gaccactacc agcagaacac ccccatcggc gacggccccg tgctgctgcc   3660
cgacaaccac tacctgagca cccagtccgc cctgagcaaa gaccccaacg agaagcgcga   3720
tcacatggtc ctgctggagt tcgtgaccgc cgccgggatc actctcggca tggacgagct   3780
gtacaagatg gacccagaac gacgcccggc cgacatccgc cgtgccaccg aggcggacat   3840
gccggcggtc tgcaccatcg tcaaccacta catcgagaca agcacggtca acttccgtac   3900
cgagccgcag gaaccgcagg agtggacgga cgacctcgtc cgtctgcggg agcgctatcc   3960
ctggctcgtc gccgaggtgg acggcgaggt cgccggcatc gcctacgcgg gccctggaa    4020
ggcacgcaac gcctacgact ggacggccga gtcgaccgtg tacgtctccc ccgccacca    4080
gcggacggga ctgggctcca cgctctacac ccacctgctg aagtccctgg aggcacaggg   4140
cttcaagagc gtggtcgctg tcatcgggct gcccaacgac ccgagcgtgc gcatgcacga   4200
ggcgctcgga tatgcccccc gcggcatgct gcgggcggcc ggcttcaagc acgggaactg   4260
gcatgacgtg ggtttctggc agctggactt cagcctgccg gtaccgcccc gtccggtcct   4320
gcccgtcacc gagatctgag ctagcacgcg tctaggatcc gaagcagatc gttcaaacat   4380
ttggcaataa agtttcttaa gattgaatcc tgttgccggt cttgcgatga ttatcatata   4440
atttctgttg aattacgtta agcatgtaat aattaacatg taatgcatga cgttatttat   4500
gagatgggtt tttatgatta gagtcccgca attatacatt taatacgcga tagaaaacaa   4560
aatatagcgc gcaaactagg ataaattatc gcgcgcggtg tcatctatgt tactagatcg   4620
ggaagatcct ctagatacgt agcgatcgcc atggagccat ttacaattga atatatcctg   4680
ccg                                                                 4683
```

```
<210> SEQ ID NO 5
<211> LENGTH: 4992
<212> TYPE: DNA
<213> ORGANISM: Artificial Sequence
<220> FEATURE:
<223> OTHER INFORMATION: T-DNA of pTCV64
<220> FEATURE:
<221> NAME/KEY: misc_feature
<222> LOCATION: (191)..(222)
<223> OTHER INFORMATION: Right T-DNA border
<220> FEATURE:
<221> NAME/KEY: promoter
<222> LOCATION: (270)..(818)
<223> OTHER INFORMATION: CaMV35S promoter fragment
<220> FEATURE:
<221> NAME/KEY: misc_feature
<222> LOCATION: (819)..(875)
<223> OTHER INFORMATION: cab22Leader fragment
<220> FEATURE:
<221> NAME/KEY: misc_feature
<222> LOCATION: (885)..(1553)
<223> OTHER INFORMATION: 5' part of eGFP coding region
<220> FEATURE:
<221> NAME/KEY: misc_feature
<222> LOCATION: (1554)..(1571)
<223> OTHER INFORMATION: I-SceI recognition site
<220> FEATURE:
<221> NAME/KEY: misc_feature
<222> LOCATION: (1573)..(1581)
<223> OTHER INFORMATION: Zif268 recognition site
<220> FEATURE:
<221> NAME/KEY: terminator
<222> LOCATION: (1595)..(1833)
<223> OTHER INFORMATION: 3' 35S transcription termination and
      polyadenylation region (complement)
<220> FEATURE:
<221> NAME/KEY: misc_feature
<222> LOCATION: (1845)..(2870)
<223> OTHER INFORMATION: hygromycin phosphotransferase coding region
<220> FEATURE:
<221> NAME/KEY: misc_feature
<222> LOCATION: (2877)..(2949)
<223> OTHER INFORMATION: leader of CsVMV (complement)
<220> FEATURE:
<221> NAME/KEY: promoter
<222> LOCATION: (2950)..(3389)
<223> OTHER INFORMATION: CsVMV promoter fragment (complement)
<220> FEATURE:
<221> NAME/KEY: misc_feature
<222> LOCATION: (3431)..(4096)
<223> OTHER INFORMATION: 3' part of eGFP coding region
<220> FEATURE:
<221> NAME/KEY: misc_feature
<222> LOCATION: (4097)..(4648)
<223> OTHER INFORMATION: phosphinotricin acetyltransferase coding region
<220> FEATURE:
<221> NAME/KEY: terminator
<222> LOCATION: (4650)..(4858)
<223> OTHER INFORMATION: 3'nos: transcription termination and
      polyadenylation region of the nopaline synthase gene
<220> FEATURE:
<221> NAME/KEY: misc_feature
<222> LOCATION: (4968)..(4992)
<223> OTHER INFORMATION: Left T-DNA border sequence

<400> SEQUENCE: 5
agattcgaag ctcggtcccg tgggtgttct gtcgtctcgt tgtacaacga aatccattcc      60
cattccgcgc tcaagatggc ttcccctcgg cagttcatca gggctaaatc aatctagccg     120
acttgtccgg tgaaatgggc tgcactccaa cagaaacaat caaacaaaca tacacagcga     180
cttattcaca cgcgacaaat tacaacggta tatatcctgc cagtactcgg ccgtcgacct     240
gcaggcaatt ggtacctacg tatgcatggc gcgccatatg caccatacat ggagtcaaaa     300
attcagatcg aggatctaac agaactcgcc gtgaagactg gcgaacagtt catacagagt     360
cttttacgac tcaatgacaa gaagaaaatc ttcgtcaaca tggtggagca cgacactctc     420
```

```
gtctactcca agaatatcaa agatacagtc tcagaagacc aaagggctat tgagactttt    480
caacaaaggg taatatcggg aaacctcctc ggattccatt gcccagctat ctgtcacttc    540
atcaaaagga cagtagaaaa ggaaggtggc acctacaaat gccatcattg cgataaagga    600
aaggctatcg ttcaagatgc ctctgccgac agtggtccca agatggaccc ccacccacg    660 aggagcatcg tggaaaaaga agacgttcca accacgtctt caaagcaagt ggattgatgt    720
gatatctcca ctgacgtaag ggatgacgca caatcccact atccttcgca agacccttcc    780
tctatataag gaagttcatt tcatttggag aggactcgag ctcatttctc tattacttca    840
gccataacaa aagaactctt ttctcttctt attaaaccaa aaccatggtg agcaagggcg    900
aggagctgtt caccggggtg gtgcccatcc tggtcgagct ggacggcgac gtaaacggcc    960
acaagttcag cgtgtccggc gagggcgagg gcgatgccac ctacggcaag ctgaccctga   1020
agttcatctg caccaccggc aagctgcccg tgccctggcc caccctcgtg accaccctga   1080
cctacggcgt gcagtgcttc agccgctacc ccgaccacat gaagcagcac gacttcttca   1140
agtccgccat gcccgaaggc tacgtccagg agcgcaccat cttcttcaag gacgacggca   1200
actacaagac ccgcgccgag gtgaagttcg agggcgacac cctggtgaac cgcatcgagc   1260
tgaagggcat cgacttcaag gaggacggca acatcctggg gcacaagctg gagtacaact   1320
acaacagcca caacgtctat atcatggccg acaagcagaa gaacggcatc aaggtgaact   1380
tcaagatccg ccacaacatc gaggacggca gcgtgcagct cgccgaccac taccagcaga   1440
acacccccat cggcgacggc cccgtgctgc tgcccgacaa ccactacctg agcacccagt   1500
ccgccctgag caaagacccc aacgagaagc gcgatcacat ggtcctgctg gagtagggat   1560
aacagggtaa tggcgtgggc gaccggtccc ggccgctgta ccatgcatga tctggatttt   1620
agtactggat tttggtttta ggaattagaa attttattga tagaagtatt ttacaaatac   1680
aaatacatac taagggtttc ttatatgctc aacacatgag cgaaaccca taggaaccct   1740 aattccctta tctgggaact actcacacat tattatggag aaaatagaga gagatagatt   1800
tgtagagaga gactggtgat ttcagcgtgt ccaagcttga tatcctattc ctttgccctc   1860
ggacgagtgc tggggcgtcg gtttccacta tcggcgagta cttctacaca gccatcggtc   1920
cagacggccg cgcttctgcg ggcgatttgt gtacgcccga cagtcccggc tccggatcgg   1980
acgattgcgt cgcatcgacc ctgcgcccaa gctgcatcat cgaaattgcc gtcaaccaag   2040
ctctgataga gttggtcaag accaatgcgg agcatatacg cccggagccg cggcgatcct   2100
gcaagctccg gatgcctccg ctcgaagtag cgcgtctgct gctccataca agccaaccac   2160
ggcctccaga agaagatgtt ggcgacctcg tattgggaat ccccgaacat cgcctcgctc   2220
cagtcaatga ccgctgttat gcggccattg tccgtcagga cattgttgga gccgaaatcc   2280
gcgtgcacga ggtgccggac ttcggggcag tcctcggccc aaagcatcag ctcatcgaga   2340
gcctgcgcga cggacgcact gacggtgtcg tccatcacag tttgccagtg atacacatgg   2400
ggatcagcaa tcgcgcatat gaaatcacgc catgtagtgt attgaccgat tccttgcggt   2460
ccgaatgggc cgaacccgct cgtctggcta agatcggccg cagcgatcgc atccatggcc   2520
tccgcgaccg gctgcagaac agcgggcagt tcggtttcag gcaggtcttg caacgtgaca   2580
ccctgtgcac ggcgggagat gcaataggtc aggctctcgc tgaattcccc aatgtcaagc   2640
acttccggaa tcgggagcgc ggccgatgca agtgccgat aaacataacg atctttgtag   2700
aaaccatcgg cgcagctatt tacccgcagg acatatccac gccctcctac atcgaagctg   2760
aaagcacgag attcttcgcc ctccgagagc tgcatcaggt cggagacgct gtcgaacttt   2820
```

-continued

```
tcgatcagaa acttctcgac agacgtcgcg gtgagttcag gcttttcat ctcgagacaa        2880 acttacaaat ttctctgaag ttgtatcctc agtacttcaa agaaaatagc ttacaccaaa        2940
ttttttcttg ttttcacaaa tgccgaactt ggttccttat ataggaaaac tcaagggcaa        3000
aaatgacacg gaaaaatata aaggataag tagtggggga taagattcct ttgtgataag         3060
gttactttcc gcccttacat tttccacctt acatgtgtcc tctatgtctc tttcacaatc        3120 accgaccta tcttcttctt ttcattgttg tcgtcagtgc ttacgtcttc aagattcttt         3180
tcttcgcctg gttcttcttt ttcaatttct acgtattctt cttcgtattc tggcagtata        3240
ggatcttgta tctgtacatt cttcattttt gaacataggt tgcatatgtg ccgcatattg        3300
atctgcttct tgctgagctc acataatact tccatagttt ttcccgtaaa cattggattc        3360
ttgatgctac atcttggata attaccttcg gcgcgccatg catacgtagg taccaattgc        3420
cgggaccggt gagctggacg gcgacgtaaa cggccacaag ttcagcgtgt ccggcgaggg        3480
cgagggcgat gccacctacg gcaagctgac cctgaagttc atctgcacca ccggcaagct        3540
gcccgtgccc tggcccaccc tcgtgaccac cctgacctac ggcgtgcagt gcttcagccg        3600
ctaccccgac cacatgaagc agcacgactt cttcaagtcc gccatgcccg aaggctacgt        3660
ccaggagcgc accatcttct tcaaggacga cggcaactac aagacccgcg ccgaggtgaa        3720
gttcgagggc gacacccctgg tgaaccgcat cgagctgaag gcatcgact tcaaggagga        3780 cggcaacatc ctgggcaca agctggagta caactacaac agccacaacg tctatatcat        3840
ggccgacaag cagaagaacg gcatcaaggt gaacttcaag atccgccaca acatcgagga        3900
cggcagcgtg cagctcgccg accactacca gcagaacacc cccatcggcg acggccccgt        3960
gctgctgccc gacaaccact acctgagcac ccagtccgcc ctgagcaaag accccaacga        4020
gaagcgcgat cacatggtcc tgctggagtt cgtgaccgcc gccgggatca ctctcggcat        4080
ggacgagctg tacaagatgg acccagaacg acgcccggcc gacatccgcc gtgccaccga        4140
ggcggacatg ccggcggtct gcaccatcgt caaccactac atcgagacaa gcacggtcaa        4200
cttccgtacc gagccgcagg aaccgcagga gtggacggac gacctcgtcc gtctgcggga        4260
gcgctatccc tggctcgtcg ccgaggtgga cggcgaggtc gccggcatcg cctacgcggg        4320
cccctggaag gcacgcaacg cctacgactg gacggccgag tcgaccgtgt acgtctcccc        4380
ccgccaccag cggacgggac tgggctccac gctctacacc cacctgctga gtccctgga        4440 ggcacagggc ttcaagagcg tggtcgctgt catcgggctg cccaacgacc cgagcgtgcg        4500
catgcacgag gcgctcggat atgcccccg cggcatgctg cggcggccg gcttcaagca        4560 cgggaactgg catgacgtgg gtttctggca gctggacttc agcctgccgg taccgccccg        4620
tccggtcctg cccgtcaccg agatctgagc tagcacgcgt ctaggatccg aagcagatcg        4680
ttcaaacatt tggcaataaa gtttcttaag attgaatcct gttgccgtc ttgcgatgat         4740 tatcatataa tttctgttga attacgttaa gcatgtaata ttaacatgt aatgcatgac          4800 gttatttatg agatgggttt ttatgattag agtcccgcaa ttatacattt aatacgcgat        4860
agaaaacaaa atatagcgcg caaactagga taaattatcg cgcgcggtgt catctatgtt        4920
actagatcgg gaagatcctc tagatacgta gcgatcgcca tggagccatt tacaattgaa        4980
tatatcctgc cg                                                            4992
```

<210> SEQ ID NO 6
<211> LENGTH: 3987
<212> TYPE: DNA
<213> ORGANISM: Artificial Sequence

```
<220> FEATURE:
<223> OTHER INFORMATION: T-DNA of pTCV72
<220> FEATURE:
<221> NAME/KEY: misc_feature
<222> LOCATION: (191)..(222)
<223> OTHER INFORMATION: right T-DNA border
<220> FEATURE:
<221> NAME/KEY: terminator
<222> LOCATION: (251)..(539)
<223> OTHER INFORMATION: 3'ocs: transcription termination and
      polyadenylation region from an octopine synthase gene (complement)
<220> FEATURE:
<221> NAME/KEY: misc_feature
<222> LOCATION: (713)..(1510)
<223> OTHER INFORMATION: neomycin phosphotransferase II coding region
      (complement)
<220> FEATURE:
<221> NAME/KEY: misc_feature
<222> LOCATION: (1511)..(1529)
<223> OTHER INFORMATION: linker sequence
<220> FEATURE:
<221> NAME/KEY: promoter
<222> LOCATION: (1530)..(1816)
<223> OTHER INFORMATION: nopaline synthase promoter fragment
      (complement)
<220> FEATURE:
<221> NAME/KEY: misc_feature
<222> LOCATION: (1817)..(1929)
<223> OTHER INFORMATION: linker sequence
<220> FEATURE:
<221> NAME/KEY: promoter
<222> LOCATION: (1941)..(2926)
<223> OTHER INFORMATION: promoter fragment from NTM19 gene from tobacco
<220> FEATURE:
<221> NAME/KEY: transit_peptide
<222> LOCATION: (2928)..(2961)
<220> FEATURE:
<221> NAME/KEY: misc_feature
<222> LOCATION: (2962)..(3661)
<223> OTHER INFORMATION: I-SceI coding region
<220> FEATURE:
<221> NAME/KEY: terminator
<222> LOCATION: (3665)..(3913)
<223> OTHER INFORMATION: 3' 35S transcription termination and
      polyadenylation fragment
<220> FEATURE:
<221> NAME/KEY: misc_feature
<222> LOCATION: (3963)..(3987)
<223> OTHER INFORMATION: T-DNA left border region

<400> SEQUENCE: 6
agattcgaag ctcggtcccg tgggtgttct gtcgtctcgt tgtacaacga aatccattcc    60
cattccgcgc tcaagatggc ttcccctcgg cagttcatca gggctaaatc aatctagccg   120
acttgtccgg tgaaatgggc tgcactccaa cagaaacaat caaacaaaca tacacagcga   180
cttattcaca cgcgacaaat tacaacggta tatatcctgc cagtactcgg ccgtcgacct   240
gcaggcaatt gtttgttatt gtggcgctct atcatagatg tcgctataaa cctattcagc   300
acaatatatt gttttcattt taatattgta catataagta gtagggtaca atcagtaaat   360
tgaacggaga atattattca taaaaatacg atagtaacgg gtgatatatt cattagaatg   420
aaccgaaacc ggcggtaagg atctgagcta cacatgctca ggttttttac aacgtgcaca   480
acagaattga aagcaaatat catgcgatca taggcgtctc gcatatctca ttaaagcagg   540 ggtgggcga  agaactccag catgagatcc ccgcgctgga ggatcatcca gccggcgtcc   600
cggaaaacga ttccgaagcc caacctttca tagaaggcgg cggtggaatc gaaatctcgt   660
gatggcaggt tgggcgtcgc ttggtcggtc atttcgaacc ccagagtccc gctcagaaga   720
actcgtcaag aaggcgatag aaggcgatgc gctgcgaatc gggagcggcg ataccgtaaa   780
gcacgaggaa gcggtcagcc cattcgccgc caagctcttc agcaatatca cgggtagcca   840
```

| | |
|---|---|
| acgctatgtc ctgatagcgg tccgccacac ccagccggcc acagtcgatg aatccagaaa | 900 |
| agcggccatt ttccaccatg atattcggca agcaggcatc gccatgggtc acgacgagat | 960 |
| cctcgccgtc gggcatgcgc gccttgagcc tggcgaacag ttcggctggc gcgagcccct | 1020 |
| gatgctcttc gtccagatca tcctgatcga caagaccggc ttccatccga gtacgtgctc | 1080 |
| gctcgatgcg atgtttcgct tggtggtcga atgggcaggt agccggatca agcgtatgca | 1140 |
| gccgccgcat tgcatcagcc atgatggata ctttctcggc aggagcaagg tgagatgaca | 1200 |
| ggagatcctg ccccggcact cgcccaata gcagccagtc ccttcccgct tcagtgacaa | 1260 |
| cgtcgagcac agctgcgcaa ggaacgcccg tcgtggccag ccacgatagc cgcgctgcct | 1320 |
| cgtcctgcag ttcattcagg gcaccggaca ggtcggtctt gacaaaaaga accgggcgcc | 1380 |
| cctgcgctga cagccggaac acggcggcat cagagcagcc gattgtctgt tgtgcccagt | 1440 |
| catagccgaa tagcctctcc acccaagcgg ccggagaacc tgcgtgcaat ccatcttgtt | 1500 |
| caatccacat gatcatgggc cggatctttg attgagagtg aatatgagac tctaattgga | 1560 |
| taccgagggg aatttatgga acgtcagtgg agcattttg acaagaaata tttgctagct | 1620 |
| gatagtgacc ttaggcgact tttgaacgcg caataatggt ttctgacgta tgtgcttagc | 1680 |
| tcattaaact ccagaaaccc gcggctgagt ggctccttca atcgttgcgg ttctgtcagt | 1740 |
| tccaaacgta aaacggcttg tcccgcgtca tcggcggggg tcataacgtg actcccttaa | 1800 |
| ttctccgctc atgatcctgt ttcctgtgtg aaattgttat ccgctcacaa ttccacacat | 1860 |
| tatacgagcc ggaagcataa agtgtaaagc ctggggtgcc taatgagtga gaattgacgg | 1920 |
| gatctatggc gcgccatatg agatttatag ggtcctaatg cgggtactga acaccaggtg | 1980 |
| ggaaacaaaa aatatacaga acaactcctt tagaatttac aattttgag cgtgttggct | 2040 |
| tggtacgatt ctacttttca tatctctcgt catctcctaa ctcctatggt tcaccagcca | 2100 |
| ccgattaatt atgacaccgc taacaaaaat cttgcgacga cattgagaga aatttctttt | 2160 |
| cataaattgg taattcgtac atcatttata ggcgttagct ataacctttt agttagtgaa | 2220 |
| tacaatactt tttgctatta ttatgtaact tttagatatg aatttacttt caaaaaaaaa | 2280 |
| aaaaggatcg atgttggtta tcaactaagg accaaccact ttggacgtct caccactaag | 2340 |
| ttaataaaat cactttgttc tcgaaaaaaa ccccaaaagt gttaaaatgc ttttcatatc | 2400 |
| ataatcaaac aacgtgatta ataaaatcta ttaagttaat agaagtaggg aataaatcgg | 2460 |
| gcaaagaat ttgatacaaa ccaaaccggt caaaaaagct agtattcata taaatggact | 2520 |
| atacaagtta ataccagcta gcagaaatta aatagtttat taagttgatt acaaaacaat | 2580 |
| tcctcattta aaaaagtta atgtaatcaa gagatctttt gcttctaatt gatcagacga | 2640 |
| ggaccctct tatttatttt cttttcata taagattttg aatagatata gggaaatctt | 2700 |
| gttcactctt tatctacttc aaattgcatg cattttaaga attctctttg tatgcaaact | 2760 |
| tcagtattta tgattgacat aaatcaatat tcatatcttc gataaagtta ataactctcc | 2820 |
| taatacttat gaatatctct tcctttacaa ccctataaaa ccccccacta tagctacctt | 2880 |
| cataattcat cttagagtac caaccctaaa tttcttagtg attaaccatg gctaaacccc | 2940 |
| ccaagaagaa gcgcaaggtt aacatcaaaa aaaaccaggt aatgaacctg gtccgaact | 3000 |
| ctaaactgct gaaagaatac aaatcccagc tgatcgaact gaacatcgaa cagttcgaag | 3060 |
| caggtatcgg tctgatcctg ggtgatgctt acatccgttc tcgtgatgaa ggtaaaacct | 3120 |
| actgtatgca gttcgagtgg aaaaacaaag catacatgga ccacgtatgt ctgctgtacg | 3180 |
| atcagtgggt actgtccccg ccgcacaaaa agaacgtgt taaccacctg ggtaacctgg | 3240 |

-continued

```
taatcacctg gggcgcccag actttcaaac accaagctttt caacaaactg ctaacctgt    3300 tcatcgttaa caacaaaaaa accatcccga acaacctggt tgaaaactac ctgaccccga    3360
tgtctctggc atactggttc atggatgatg gtggtaaatg ggattacaac aaaaactcta    3420
ccaacaaatc gatcgtactg aacacccagt cttttcacttt cgaagaagta gaatacctgg    3480
ttaagggtct gcgtaacaaa ttccaactga actgttacgt aaaaatcaac aaaaacaaac    3540
cgatcatcta catcgattct atgtcttacc tgatcttcta caacctgatc aaaccgtacc    3600
tgatcccgca gatgatgtac aaactgccga acactatctc ctccgaaact ttcctgaaat    3660
agggctagca agcttggaca cgctgaaatc accagtctct ctctacaaat ctatctctct    3720 ctatttctc cataataatg tgtgagtagt tcccagataa gggaattagg gttcctatag    3780
ggtttcgctc atgtgttgag catataagaa accctttagta tgtatttgta tttgtaaaat    3840
acttctatca ataaaatttc taattcctaa aaccaaaatc cagtactaaa atccagatca    3900
tgcatggtac agcggccgcg ttaacgcgta tactctagat acgtagcgat cgccatggag    3960
ccatttacaa ttgaatatat cctgccg                                         3987
```

<210> SEQ ID NO 7
<211> LENGTH: 1215
<212> TYPE: DNA
<213> ORGANISM: Brassica napus
<220> FEATURE:
<221> NAME/KEY: variation
<222> LOCATION: (151)..(151)
<223> OTHER INFORMATION: A

<400> SEQUENCE: 7

```
gatggcgcgc cgataggaat gggttggatt atacgaaata aatatggtat agttcttgac      60
tgtgaaatgg gcagatttga aggtcgaagt acagtagaag aaggtgaatg tactgcctta     120
atttgggcta tacaggcagc ttactcactg ggatacaaga aagtgatttt tgaaggtgat     180
aatatacaag tcacaagatg cttacaagct gcaagtatta acctacgatt ggagaattat     240
ctaataacta tctcggcttg gaaatctcat tttcataaca tcaggggtct gcaaattcct     300
gtgcacattt gttagcaaag aaatctttaa catccgataa tgcatggagt gtgttccata     360
cgtgttcccc atttttgtat aacaatgtca tgactggtca attaatataa aggaacttag     420
tcggaaaaaa aaatatatat cacaaagctt ctagagtctt ctacgaaata tagaatctct     480
ggaccgttat tgatacattg atcccaaatt aaaaaaagaa gatatttcaa aatctccatt     540
tatcgtatcg aatggttaat cccgaaagtt atggagtaaa ttttaaaacc ccattaattt     600
tccatattta attctccttt tccatattgt tttaggaaaa taatatttcc atattccata     660
actcacggac cgttgaatg aaaaacttta taagatggaa aaagtgttta agtgtttaaa     720
gagaaataaa ttttgtgaag aagaaaactt ttataattta gaagaggatt tttattactt     780
agatgattct tacaggatac ttcttgatga tacaaaatga aaggggagtg gaggtattta     840
tagcctccaa aatataaaat atcttacata ttttaatcct aaatctagag aattctacca     900
taatatctaa gattttttat tagaattatc tagataattc tatgagaata tctagatttt     960
tattctaagg aggtggaaga tgattctaga tattggacta agtttggact aaaatggtta    1020
gtaaattatt agcccaaaat gtgatccaaa tcaaatttaa ttttcaacac gaccctctca    1080
acattataaa taagagagac tcattccctc accaagtctc atcctcaagt ccattctaca    1140
aaacaaaacc ctagaactct tcgccgctttt taacctaact aatcaaaaca acaatgcca    1200 aaaccatggt gaaga                                                     1215
```